(12) United States Patent  (10) Patent No.: US 7,303,534 B2
Kahn  (45) Date of Patent: Dec. 4, 2007

(54) ROTATING FIRMNESS SENSOR

(76) Inventor: Rocky Kahn, 5832 Birch Ct., Oakland, CA (US) 94618

( * ) Notice: Subject to any disclaimer, the term of this patent is extended or adjusted under 35 U.S.C. 154(b) by 339 days.

(21) Appl. No.: 10/976,204

(22) Filed: Oct. 28, 2004

(65) Prior Publication Data

US 2005/0090767 A1   Apr. 28, 2005

Related U.S. Application Data

(60) Provisional application No. 60/515,134, filed on Oct. 28, 2003.

(51) Int. Cl.
*A61B 5/103* (2006.01)
(52) U.S. Cl. ...................................... 600/587
(58) Field of Classification Search ................ 600/594, 600/587, 595, 550; 73/767, 790, 818, 829
See application file for complete search history.

(56) References Cited

U.S. PATENT DOCUMENTS 4,503,865 A * 3/1985 Shishido ..................... 600/587
5,860,934 A * 1/1999 Sarvazyan .................. 600/587
6,070,472 A * 6/2000 Kipping et al. ............... 73/829

* cited by examiner

*Primary Examiner*—Max F. Hindenburg
*Assistant Examiner*—Sharick Naqi
(74) *Attorney, Agent, or Firm*—Porter, Wright, Morris & Arthur LLP

(57) ABSTRACT

A firmness tester is disclosed which conducts its test through one or more rolling indenters impinging upon the surface of a subject. Most firmness sensors require the sample to be held stationary relative to the tester's reference plane. This invention allows the tester to differentiate between the firmness of the sample and movement of the sample relative to the sensing device. This is desirable in the application of an automatic massage chair where the roller/sensor presses upon the user's back and may cause the point of contact on the user's body to move away by means of the user flexing at the hips or arching through the back. The rolling feature is desirable in the field of automated chair massage where the massage indenters slide across the user's back with significant pressure through a membrane. This membrane would wear quickly if the indenters were not equipped with such a rolling mechanism.

19 Claims, 36 Drawing Sheets

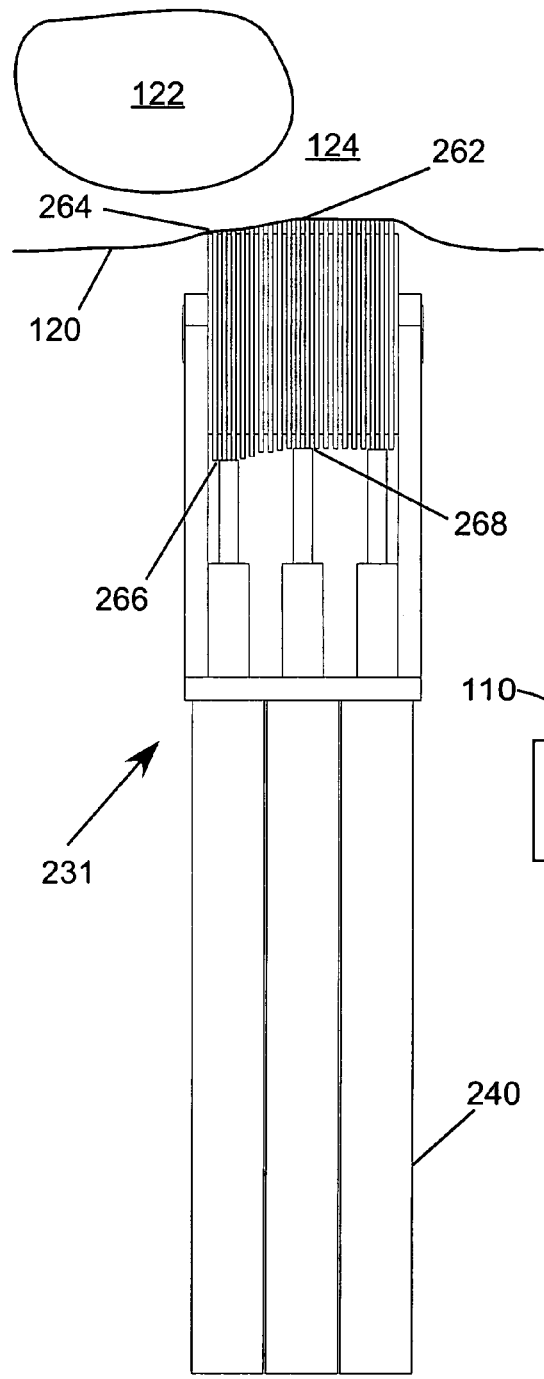
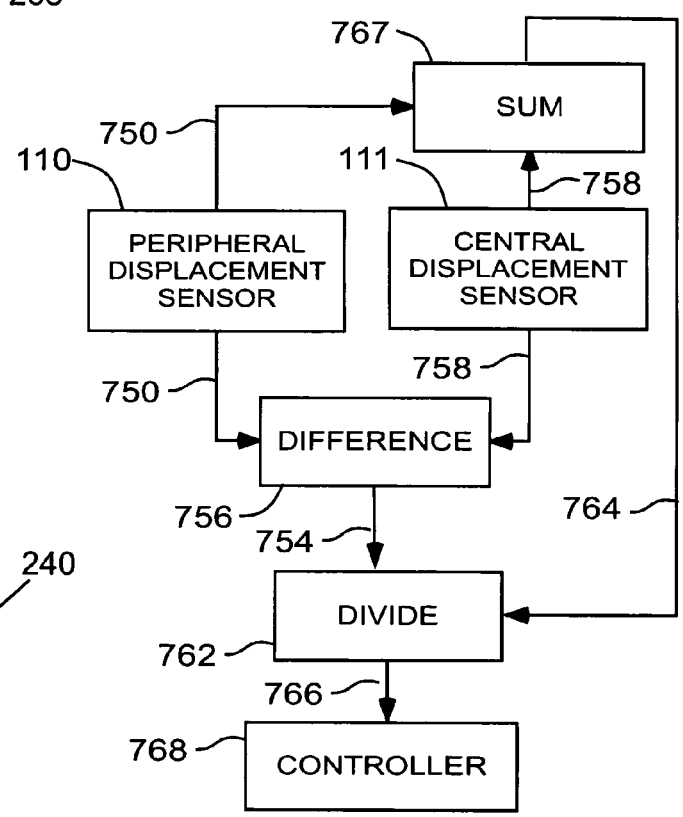
FIG. 46
FIG. 47

ROTATING FIRMNESS SENSOR

CROSS-REFERENCE TO RELATED APPLICATIONS

This application claims the benefit of U.S. Provisional Patent Application No. 60/515,134 file on Oct. 28, 2003, the disclosure of which is expressly incorporated herein in its entirety by reference.

STATEMENT REGARDING FEDERALLY SPONSORED RESEARCH

Not Applicable

REFERENCE TO MICROFICHE APPENDIX

Not Applicable

FIELD OF THE INVENTION

The invention pertains generally to the measurement of firmness of a sample and more particularly to an electromechanical firmness measurement instrument with one or more indenters in rolling contact with the sample. The implementations disclosed are most suitable for use in automatic massage chairs though this is not meant to restrict the scope of the claims.

BACKGROUND OF THE INVENTION

Quantifying muscle firmness is important in many areas of physiological research and clinical diagnosis. Specifically, quantifying muscle firmness can aid understanding of muscle operation; show the effect of physical fitness theories that have been applied to muscle groups; and enable doctors and researchers to better understand the causes of bone loss. The determining of tissue firmness is also important in the detection of heterogeneity in flesh and organs. Much research and development has gone into creating a sensor that can find breast and colon tumors by finding local differences in tissue firmness.

Many methods and instruments have been devised in the measurement of firmness. Ultrasonic and magnetic resonance imaging are popular methods but have the disadvantages of being expensive and bulky. With the objective of being able to determine firmness by "feel", the indentation or palpation of an object in conjunction with a force measurements to determine tissue firmness has been well addressed in the prior art as described below.

A muscle tonometer device is described in Roush U.S. Pat. No. 5,038,795 and reproduced as FIG. 26. It measures the firmness of a muscle by measuring the force/displacement of a tissue sample captured by a pair of calipers 416. This technique limits its scope to tissues which can be sandwiched between parts of the measurement apparatus which the present invention seeks to avoid. In particular, it is not possible to use such a device to map the structure of the user's lower back with access only to the user's dorsal side.

In two of Sarvazyan's patents; U.S. Pat. Nos. 5,524,636 and 5,833,633, and in Sarvazyan's U.S. Pat. Application No. 20020004630, a roller 406 is shown opposite a force sensing array 408 with breast tissue 410 between the roller 406 and the force sensing array 408 (FIG. 27). The roller 406 deforms the tissue sample 410 and the sensing array 408 will detect if the roller 406 passes a mass of differing elasticity in the tissue by the spatial shifting of the mass inside the tissue being examined. While Sarvazyan's invention uses a roller 406 to apply an excitation force, it has the same limitation as Roush's prior art-namely, that this technique limits its scope to tissues that can be sandwiched between parts of the measurement apparatus which the present invention seeks to avoid.

Leveque U.S. Pat. No. 4,159,640 (FIG. 29) measures the firmness of a tissue sample 410 with a single indenter 412 surrounded by an annular footed base 414 which surrounds the indenter 412. Once a prescribed foot pressure is achieved, the device captures the displacement of the indenter 412 relative to the footed base 414. This technique is useful in getting crude firmness measurements from one side of a sample but lacks the ability to capture a continuous force/indentation curve and the ability to roll across a surface. Furthermore, the described annular configuration would be difficult to adapt to rolling contact.

In Laird U.S. Pat. No. 5,833,634, one embodiment of a tissue examination device is a roller ball indenter which is used for palpating breast tissue in a search for tumors, FIG. 28. The roller ball 400 gives the benefit of facilitating movement of the probe over the tissue sample 410. This roller ball 400 is mounted with three force-instrumented biasing springs 402 in contact via cylindrical rollers 404 with the back surface of the roller ball 400. The force data measured by the biasing springs 402 is used to calculate the force vector of the reaction of the roller ball 400 being pressed and rolled over the tissue sample 410. Since these sprung force sensors 402 are behind a rigid roller ball 400, the forces experienced by the sensors 402 are undesirably coupled. The device so described can detect boundaries of areas at different heights or firmnesses but cannot measure the firmness of a homogeneous local area when the probe is wholly over that area-it can only detect boundaries between areas of different firmnesses.

Lasky U.S. Pat. No. 6,190,334 describes the imaging of breast tissue firmness with a sensor-equipped probe as shown in FIG. 30. In one embodiment the probe tip is fitted with a roller 420. This method requires that the tissue sample 410 be fixtured between the roller probe 420 and the table 418 which prevents the tissue sample 410 from moving away from the roller probe 420. This has the same limitation as Roush's prior art. In another embodiment, the sensor consists of a tactile array.

Ladeji-Osias, in her Ph.D. thesis, "The Biomechanics of Breast Palpation: Single and multi-probe indentation tests", describes a multi-prong soft tissue indenter as illustrated in FIG. 31. The three ball tips 430 contact the tissue sample while three linear differential transformer (LVDT) displacement sensors 422 measure the displacement of each of the prongs. Guide rods 428 maintain linear alignment of the outer prongs which are cantilevered to reduce the distance between the ball tips 430. A connecting frame 424 connects the three LVDT bodies 422 to a force load cell 426 which is itself mounted to a reference plane. The apparatus is designed to approximate the use of three fingers to manually palpate a breast (pg. ii). This thesis does not distinguish the advantage of a multi-prong indenter over a single-prong indenter aside from the multi-prong indenter mimicking the use of multiple fingers to manually palpate the breast tissue. They note, "To the best of our knowledge, no information on multi-probe indenters of this nature is available in the literature" (pg. 88). They note that surface friction affects measurements of friction and they experiment with use of water or Vaseline lubrication (pps. 107, 127, 136, and 139) but do not consider the use of rolling contact with the tissue sample. They note "The middle force consistently causes a larger displacement than the side forces" (pg. 70) but they fail to note that the displacement differential between the middle and the side probes is affected by the firmness of the sample.

Quantifying muscle firmness is important in automated massage. Specifically, quantifying firmness of localized regions of the back can allow a controller to adapt a massage pattern to avoid superficial bones such as the scapulae whose location varies between users. This information can also be used to concentrate on (or avoid) massaging areas with excessive muscle firmness (knots and spasms).

In Ookawa, U.S. Pat. No. 5,792,080 an automated massaging apparatus having self-adjusting massage pressure is disclosed. This invention maintains a desired massaging pressure by extending the roller towards the user until a reactive force is achieved. This mechanism accommodates the varying curvature of different users' backs whereby some users' lumbar back areas are more concave than others. However, Ookawa's invention does not measure firmness of a local area of the user's back and therefore cannot, for example, automatically accommodate itself to users with scapulae in different locations or detect muscle knots and concentrate massage on these areas.

Force/indentation measurements are also used in the rating of foams and the grading of fruit. However, the aforementioned patents and papers describe the most related prior art of which the applicant is aware. Accordingly, there is a need in the art for an improved method and apparatus for measuring firmness.

SUMMARY OF THE INVENTION

The present invention provides a method and apparatus for determining the firmness of a sample which overcomes at least some of the above-noted problems of the related art. The present invention provides an apparatus for measuring the firmness of a sample by application of the apparatus against the sample to be tested. The sample may optionally be contacted through a flexible material, such as cloth. The apparatus is comprised of at least one rolling indenter which is pressed into the sample to be assessed and a means to measure the force/displacement ratio variation across the contact patch.

From the foregoing disclosure and the following more detailed description of various preferred embodiments it will be apparent to those skilled in the art that the present invention provides a significant advance in the technology of firmness sensors. Particularly significant in this regard is the potential the invention affords for providing an apparatus that measures firmness by collecting force/indentation data in such as way as to be relatively immune to the sample moving away from an indenter and/or that allows indenters to move easily over the sample surface with rolling contact. Additional features and advantages of various preferred embodiments will be better understood in view of the detailed description provided below.

BRIEF DESCRIPTION OF THE DRAWINGS

These and further features of the present invention will be apparent with reference to the following description and drawings, wherein:

FIG. 46 is an orthogonal view of the Thin Maze Wheel assembly of FIGS. 41 to 45 pushed into a boundary between hard and soft areas of a sample;

FIG. 47 is a data flowchart for the Thin Maze Wheel assembly of FIG. 46 pushed into a boundary between hard and soft areas of a sample;

It should be understood that the drawings are not necessarily to scale and that the embodiments are sometimes illustrated by graphic symbols, phantom lines, diagrammatic representations, and fragmentary views. In certain instances, details that are not necessary for understanding the invention or which make other details difficult to perceive may have been omitted. It should be understood that the invention is not necessarily limited to the particular embodiments illustrated herein.

DETAILED DESCRIPTION OF CERTAIN PREFERRED EMBODIMENTS

The present invention is directed to determine the firmness of materials. It is known to the art that the elasticity of a material can be measured by applying a given force to a conformable material and measuring the amount of indentation into the material said force produces. Another way to measure firmness is to cause an indenter to be depressed into a material a given distance and measuring the force necessary to achieve that given indentation. These techniques are most useful when the sample being measured is fixtured or otherwise prevented from moving away from the indenter.

FIGS. 15 to 18 describe how a machine may measure the firmness of areas of a human body by measuring the force required to press a given distance. The test subject 501 is supported by a bed 504 which prevents the test subject 501 from moving away from the probe 508.

Figure 15:
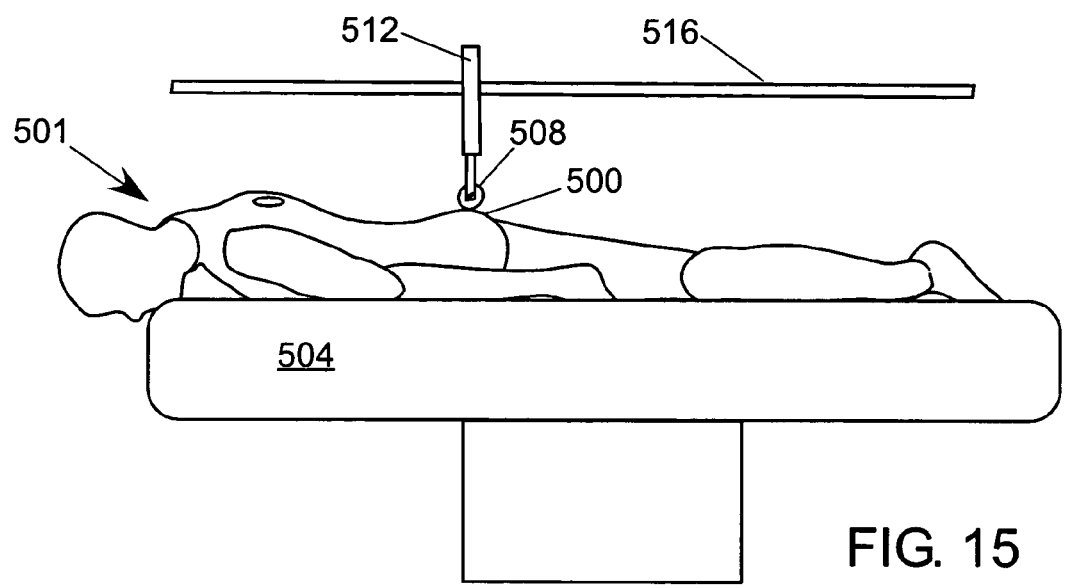
FIG. 15 is an orthogonal view of a test subject lying prone on a bed while a single roller makes initial contact with buttock flesh.
Figure 16:
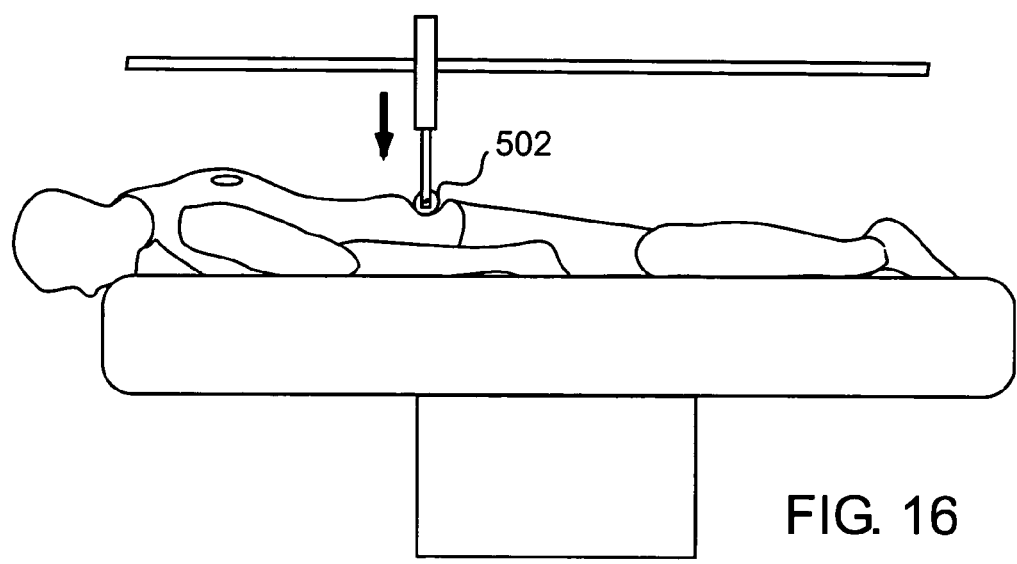
FIG. 16 is an orthogonal view of the test subject lying prone on the bed while a single roller presses into buttock flesh until reaching maximum pressing force.

In FIG. 15, a wheel probe 508 has made contact with the buttock flesh 500 of the test subject 501. In FIG. 16, the piston 512 is pressurized to a known pressure which drives it into the buttock creating a depression 502 related to the piston pressure and the softness of the buttock 500. A controller can compare the piston pressure to the depression distance 502 to determine that this contact point is relatively soft.

Figure 17:
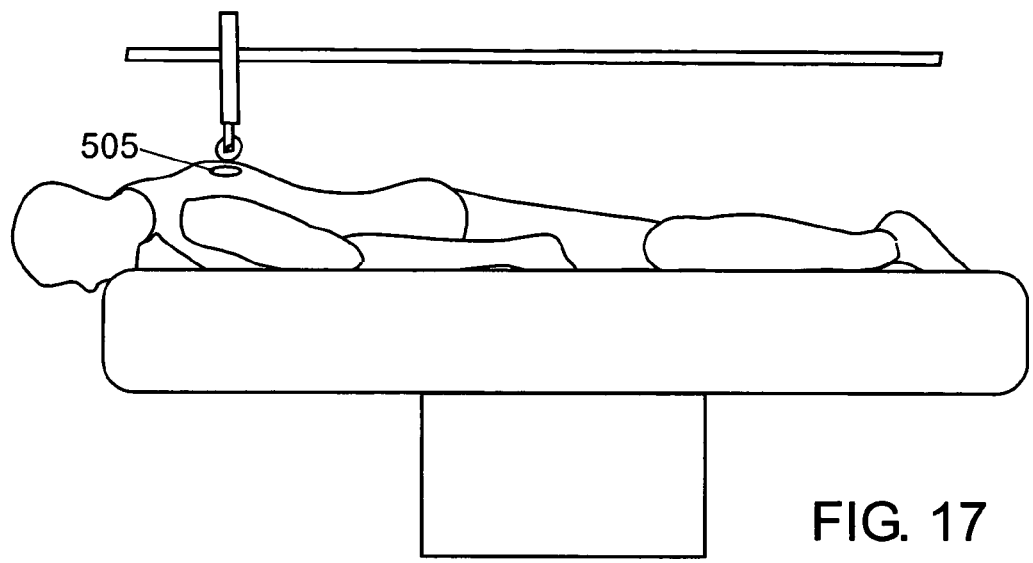
FIG. 17 is an orthogonal view of the test subject lying prone on the bed while a single roller makes initial contact with shoulder bone.
Figure 18:
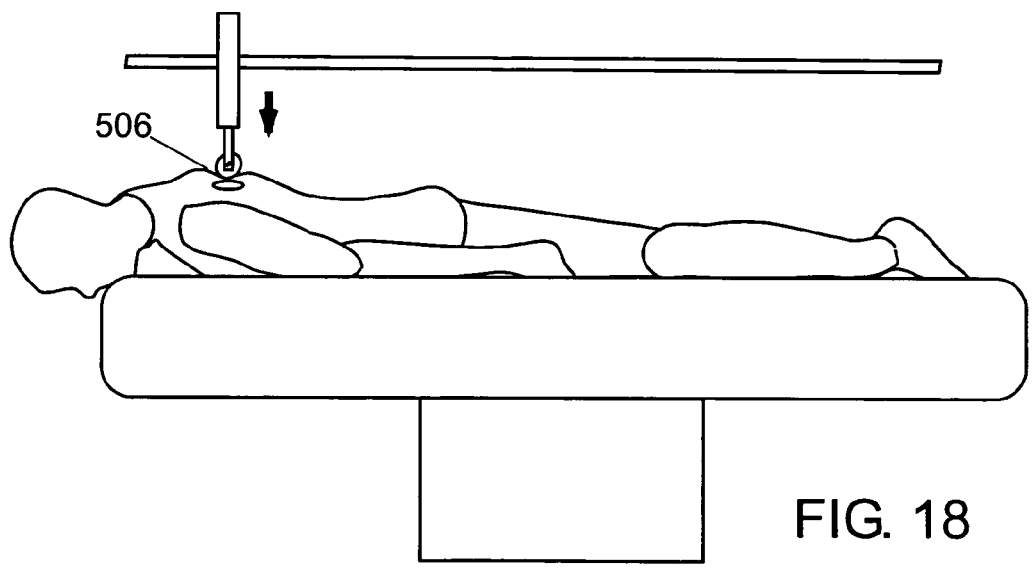
FIG. 18 is an orthogonal view of the test subject lying prone on the bed while a single roller presses into shoulder bone until reaching maximum pressing force.

FIG. 17 shows the piston 512 moved by the lead screw 516 to a position above the shoulder bone 505 of the test subject 501. In FIG. 18, as the piston 512 is pressurized to the same pressure as used above, the roller 508 is depressed into test subject 501. The depression 506 above the shoulder bone 505 is smaller than the depression 502 in the buttock 500 due to the increased firmness of the flesh supported by the shoulder bone 505. A controller can compare the piston pressure to the depression distance 506 to determine that this contact point is relatively firm.

Figure 19:
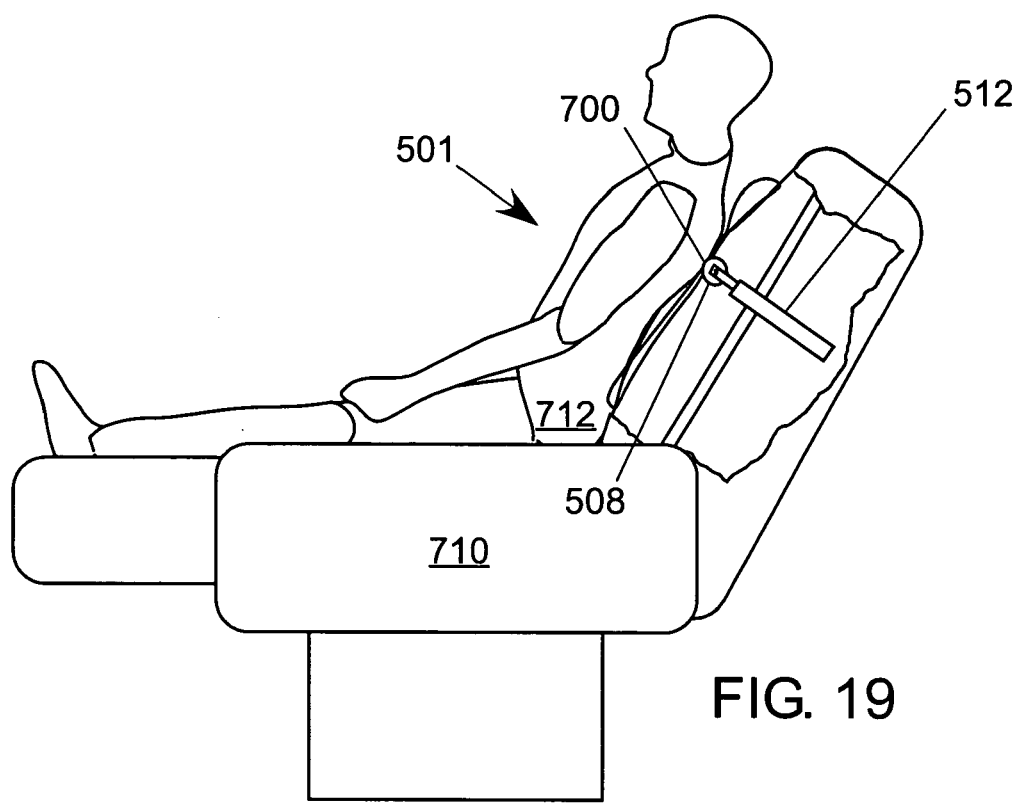
FIG. 19 is an orthogonal view of the test subject seated in a chair as a single roller makes initial contact with shoulder bone.
Figure 20:
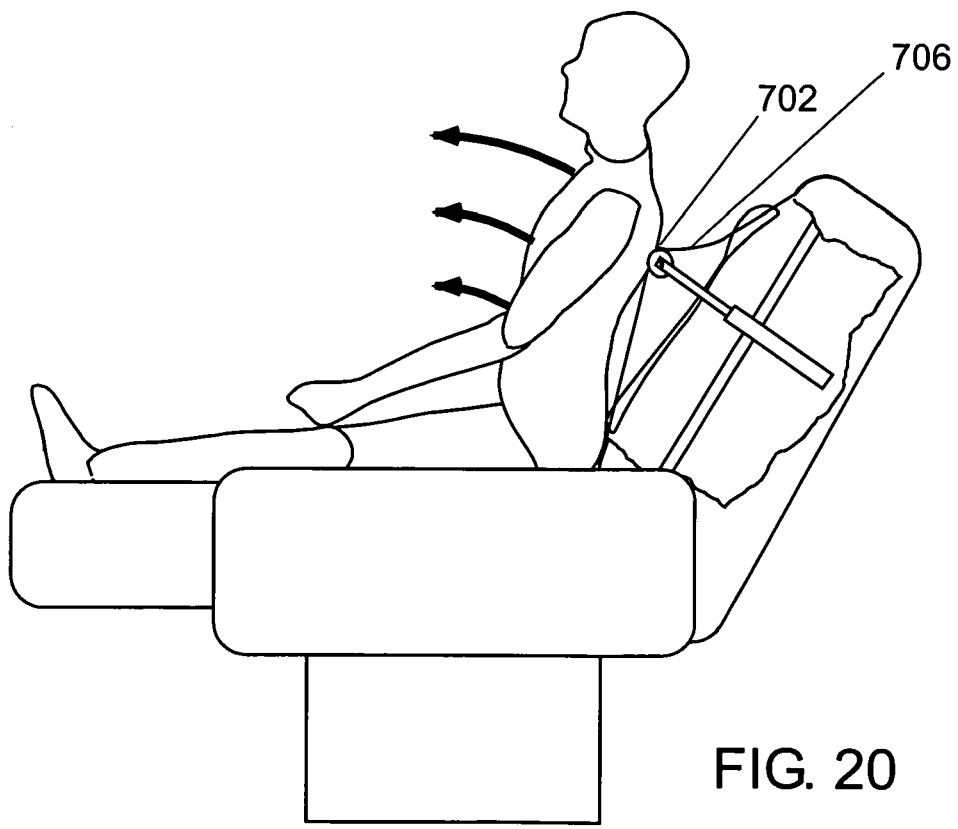
FIG. 20 is an orthogonal view of the test subject seated in chair while a single roller presses into shoulder bone causing the test subject to be pushed forward.

FIGS. 19 and 20 show a similar firmness measuring approach but this time the test subject 501 is seated in a chair 710. FIG. 19 shows the roller 508 making contact with the user's back at an initial contact point 700. FIG. 20 shows that as the piston 512 is pressurized, the roller 508 is depressed slightly into the user's back 702 but the user is passively pushed forward and bent at the user's hip 712 by the force of the roller 508. The fabric in the chair's back 706 allows the roller 508 to maintain contact during this large motion. Note that the depression into the user's back 702 is small compared to the extension of the piston 512.

Figure 21:
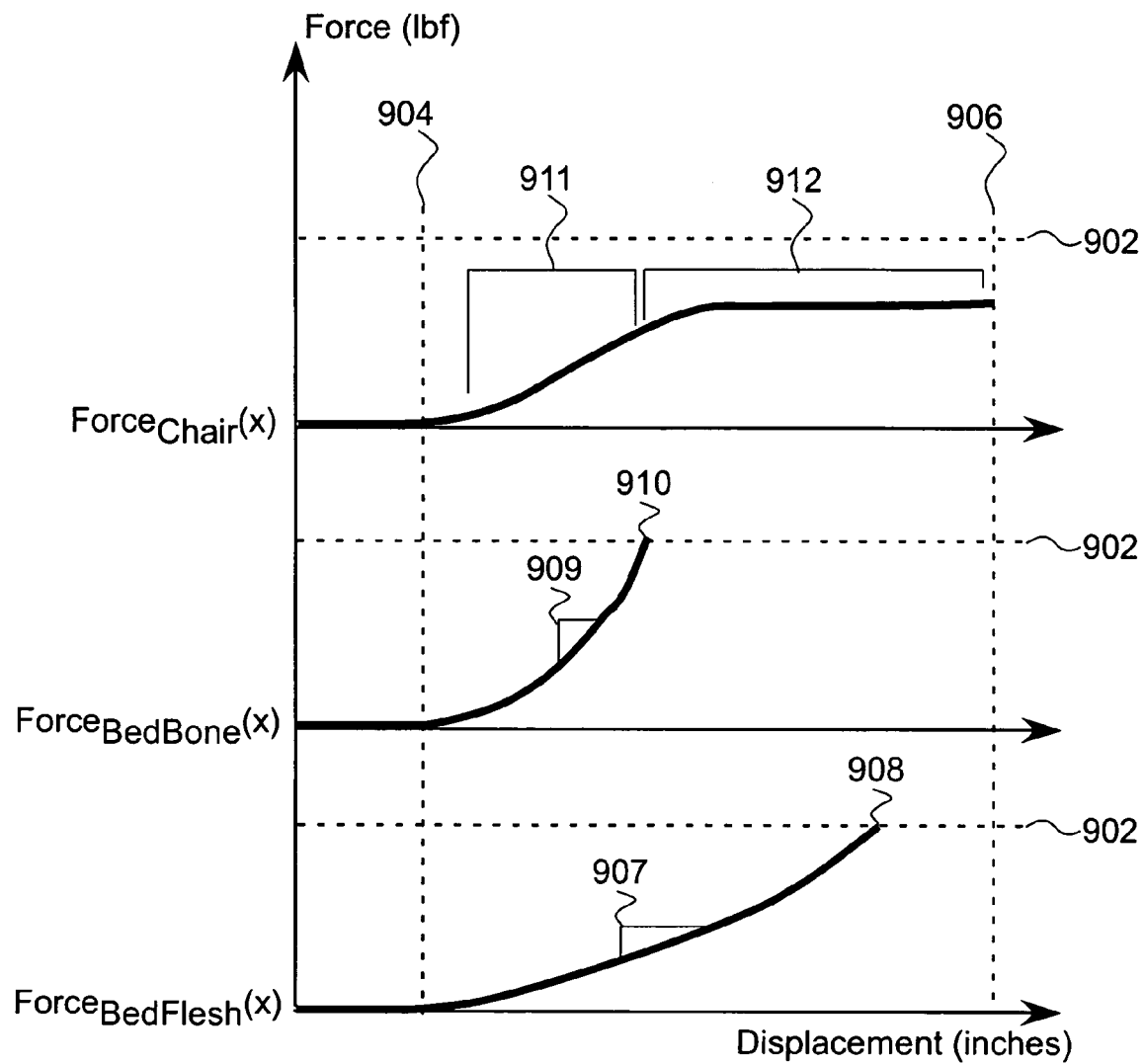
FIG. 21 is a graph showing three plots of force vs. displacement curves for a single roller with reactive force sensor.

FIG. 21 shows the force vs. displacement curves for the examples depicted in FIGS. 15 to 20.

The bottom curve, ForceBedFlesh(x), relates to FIGS. 15 and 16 and shows the force begins to increase when the roller 508 makes contact 904 with the buttock 500 of the test subject 501. Displacement increases from the contact point 904 to a maximum displacement 908 at the piston reaches the maximum test force 902. This curve increases at a medium slope 907 as the displacement increases.

The middle curve, ForceBedBone(x), relates to FIGS. 17 and 18 and shows a steeper curve 909 as the roller 508 pushes into the shoulder bone 505 of the test subject 501. The displacement 910 from contact to maximum test force 902 is less than the displacement 908 of the roller 508 when pushed into softer buttock flesh 500. Both the increased steepness of the curve and the decreased displacement indicate increased firmness.

The top curve, ForceChair(x), relates to FIGS. 19 and 20 and shows how this method is subject to artifacts of the test subject 501 moving which will confuse the determination of firmness. In this case, the test subject is seated in a chair 710 and the roller 508 makes contact with the test subject's back 700 at line 904 on the graph. Then there is a section where force increases proportionally to displacement 911. Unlike the previous examples, this curve reaches a plateau 912 where deflection increases independently of force. This occurs when the test subject 501 is pushed forward by the roller 508 and passively bends at the hip 712. A controller comparing the piston pressure to the piston extension would conclude that the contact patch is very soft which is an incorrect conclusion. These figures therefore demonstrate that when the test subject 501 is free to move away from the firmness roller 508, this method is subject to artifacts which will cause errors in firmness measurement.

One object of this invention is to create an apparatus that measures the firmness of a sample in an environment where the measurement of force/indentation is relatively immune to movement of the sample. A secondary object of this invention is to reduce friction on the sample by contacting the sample with rolling probes. This latter object is particularly important in the field of automatic massage chairs which have a layer of fabric between the mechanism and the user which would be pulled to threads if the indenters moved with sliding instead of rolling contact.

Figure 1:
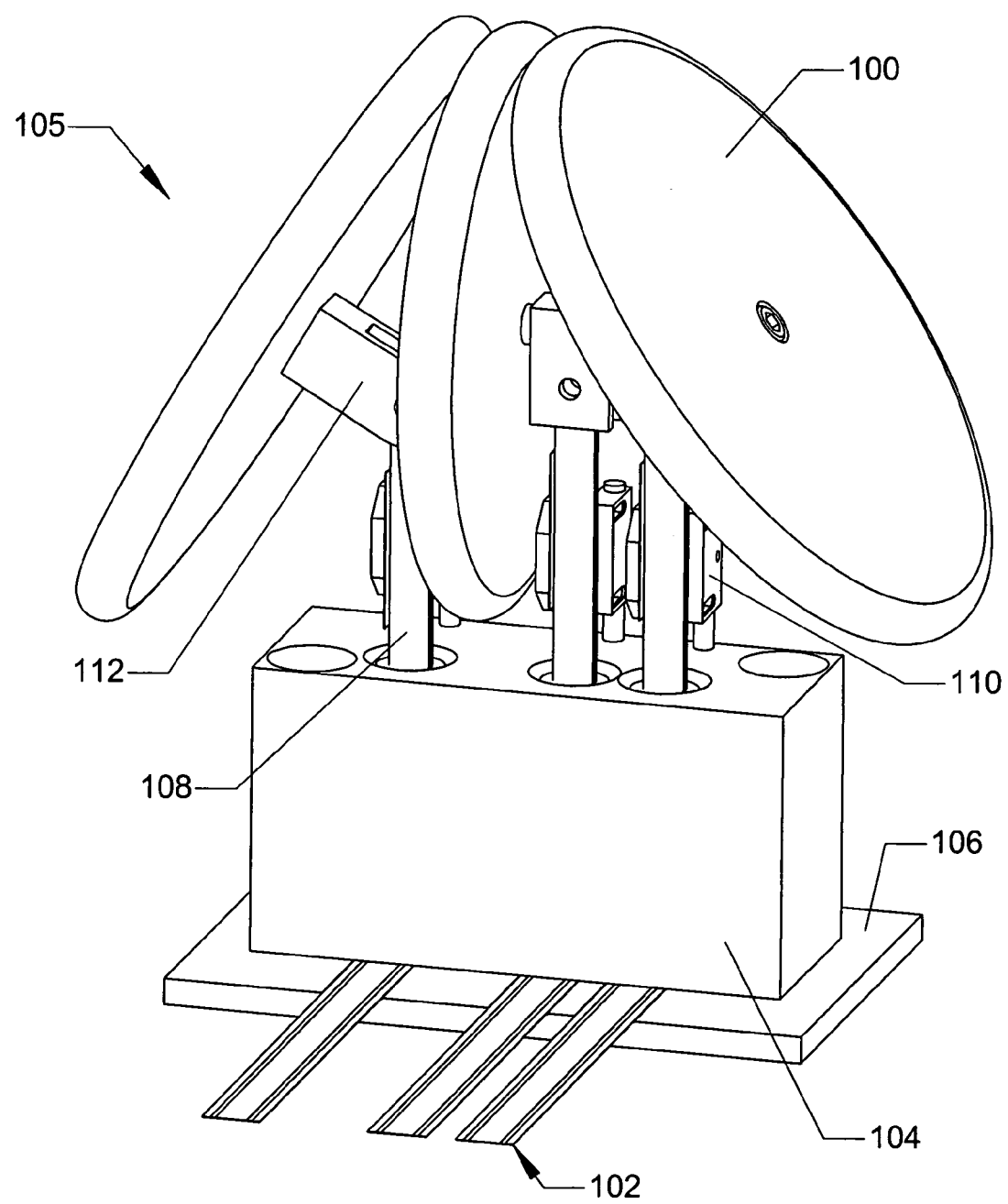
FIG. 1 is a perspective view of a Tri-Wheel implementation according to the present invention.
Figure 2:
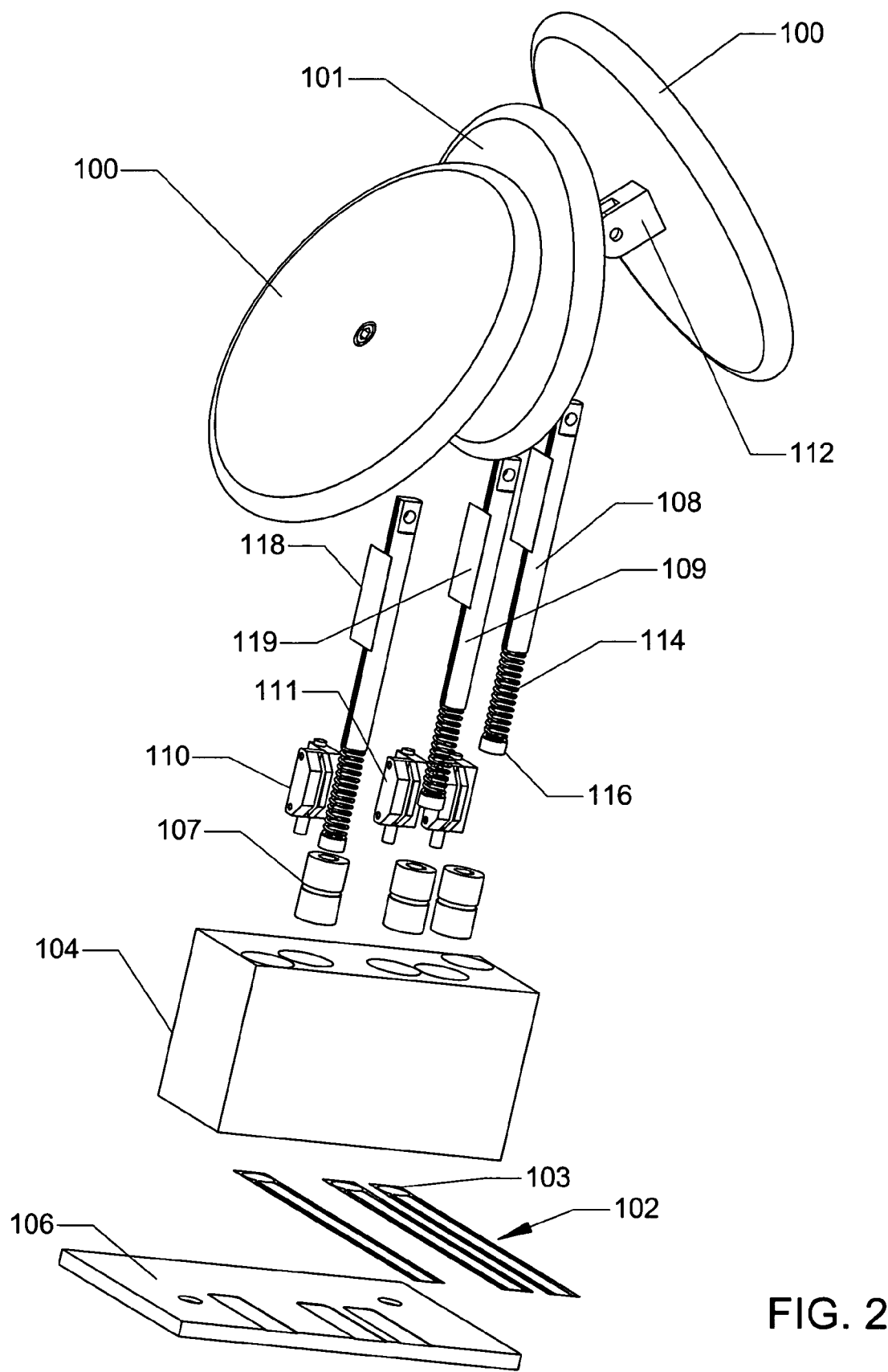
FIG. 2 is an exploded view of the Tri-Wheel implementation of FIG. 1.

FIGS. 1- to 4 show a "Tri-Wheel" embodiment of the current application. The Tri-Wheel assembly 105 has a central wheel 101 is surrounded by two peripheral wheels 100. The central wheel is supported by a central 113 yoke. The peripheral wheels are supported by peripheral 112 yokes which allow angular adjustment of the peripheral wheels 100. The yokes are mounted on central 109 and peripheral 108 spline shafts which run in spline nuts 107 which allow the spline shafts 109 and 108 to move up and down in the spline nuts 107 but prevent twisting along the shaft axes. The wheels revolve around rotational axes 126.

The spline nuts 107 are mounted in a fixture block 104. The fixture block 104 is clamped to a force sensor mounting plate 106 and three force sensors 102 such as those sold by TekScan of Boston, Mass. under the brand name FlexiForce are held between the fixture block 104 and the mounting plate 106 such that the force sensing areas 103 of the force sensors 102 are held under the axes of the spline shafts 108 and 109. Other types of force sensors such as load cells may be used instead. The spline shafts 108 and 109 are pushed away from the force sensors by springs 114. The bottoms of the springs 114 are fitted with force-diffusing slugs 116 to spread the force of the spring 114 over the force-sensing area 103 of the force sensor 102. This assembly may be mounted to some external device depending on the application. For example, this assembly may be mounted to an XYZ motion platform in a massage chair such as that described in FIGS. 19 and 20.

As force is exerted on the wheels 100 and 101, the spline shafts 108 and 109 retract into the fixture block 104. This motion causes increased compressive force on the springs 114 and force sensors 102. The magnitude of the spline shaft deflection is also measured by the peripheral 110 and central 111 encoders which detect motion of the peripheral 118 and central 119 linear encoder patterns which are mounted to the spline shafts 108 and 109.

Figure 3:
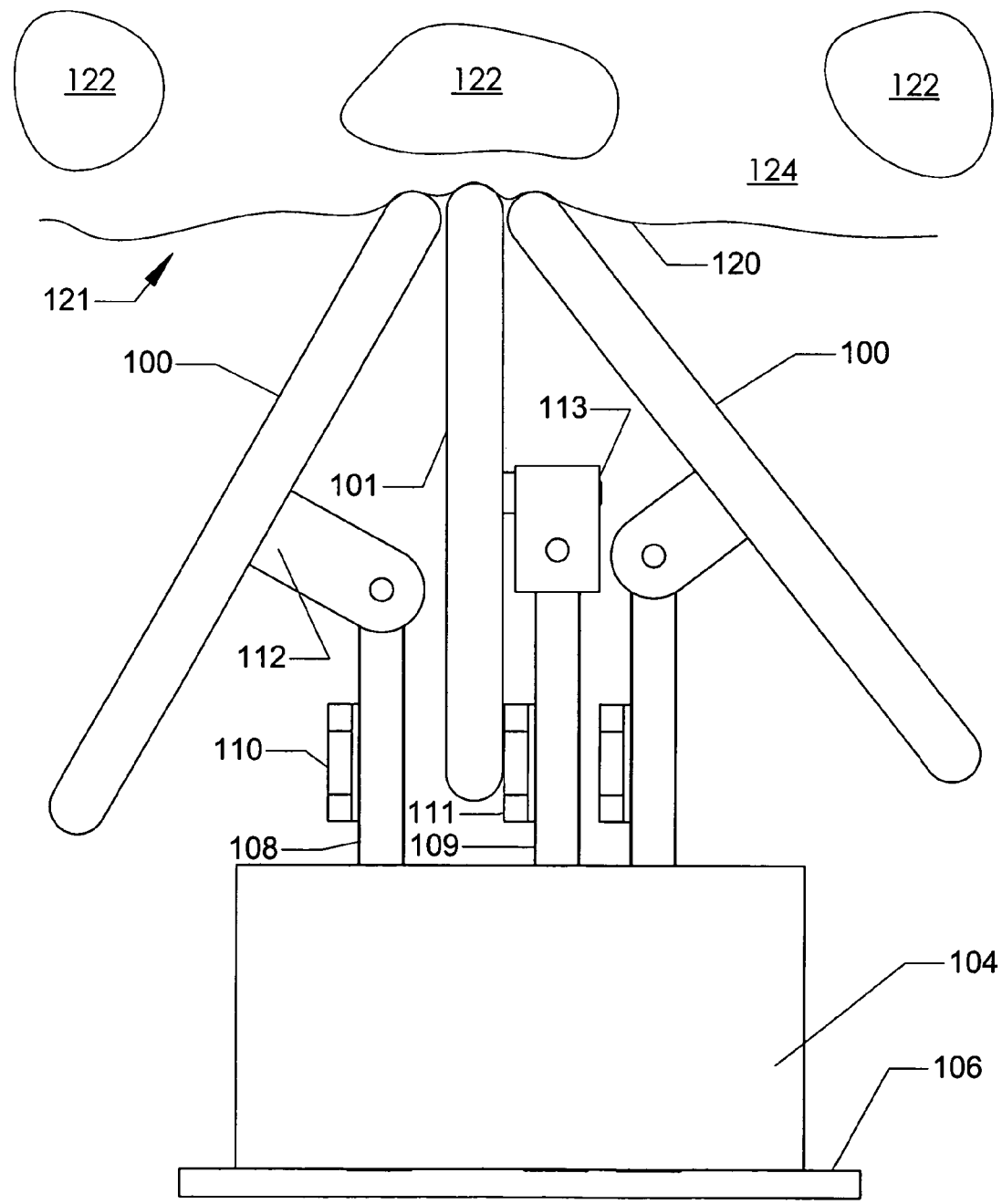
FIG. 3 is an orthogonal view of the Tri-Wheel implementation of FIGS. 1 and 2 pressing into flesh underlain with superficial bone.

Regarding FIG. 3, the tri-wheel assembly 105 is pushed into a sample 121 such as a human back consisting of a layer of skin 120 covering flesh 124 with bones 122 within. In this figure, the tri-wheel is positioned over a bone such that all three wheels are pressed into material of similar firmness at similar positions relative to the tri-wheel assembly 105. In this case, the peripheral 108 and central 109 spline shafts are pressed similar distances into the fixture block 104 so the encoders 110 and 111 measure similar displacements and three force sensors 102 measure similar forces.

Figure 4:
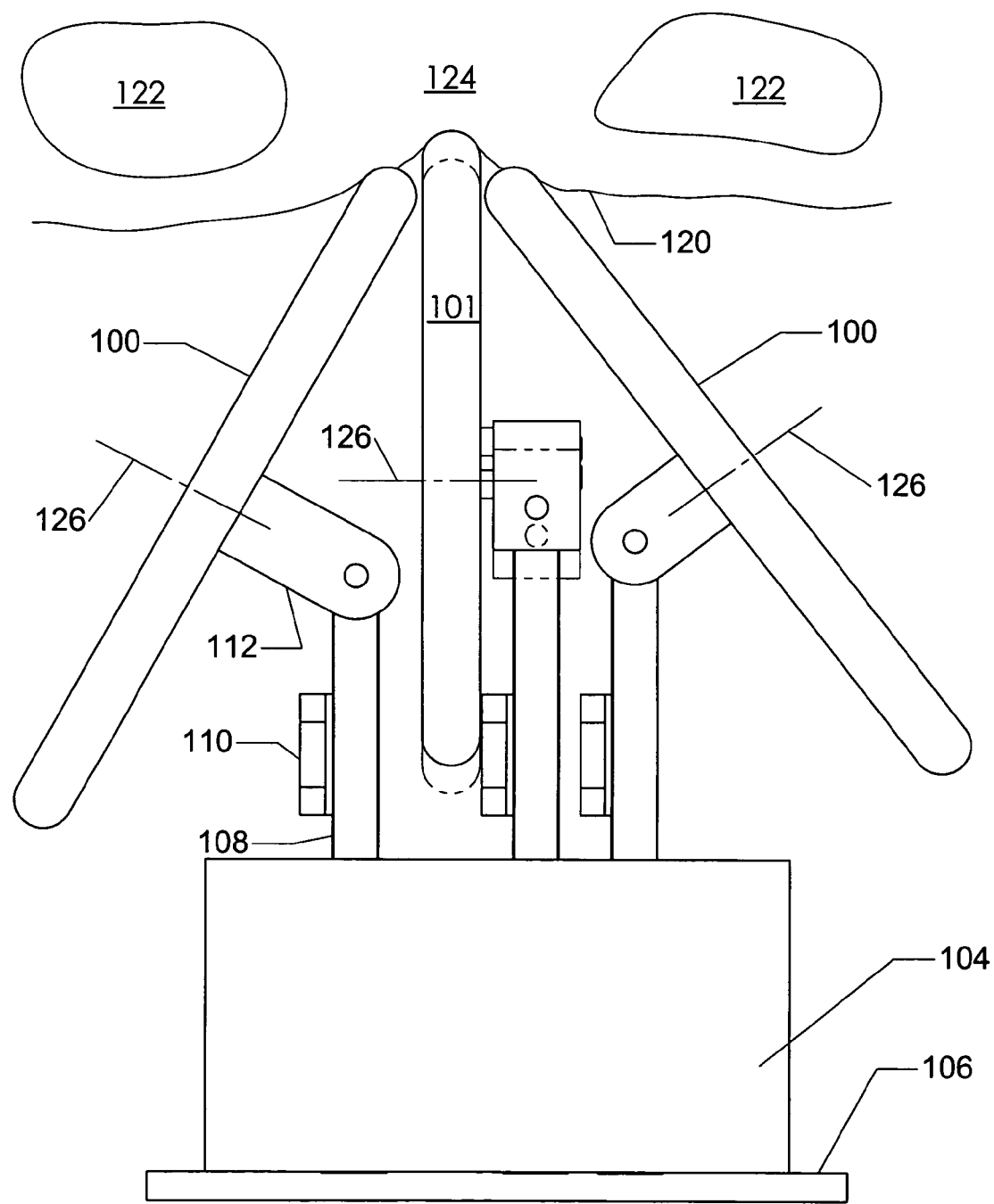
FIG. 4 is an orthogonal view of the Tri-Wheel implementation of FIGS. 1 to 3 pressing into a fleshy area of the user.

FIG. 4 shows the tri-wheel assembly 105 pushed into an area of flesh 124 without the stiffening support of underlying bones 122. If the tri-wheel assembly 105 is pushed into the sample 121 with force similar to that of FIG. 3, the central wheel 101 will push to a greater extent into the flesh 124 than the peripheral wheels 100. This is due to the peripheral wheels 100 compressing the flesh 124 and helping the central wheel 101 to penetrate deeper. This is reciprocally accomplished by the central wheel 101 compressing the flesh 124 allowing the peripheral wheels 100 to penetrate deeper so one might argue that the central and peripheral wheels 101 and 100 ought to penetrate similar distances. However, the central wheel 101 receives the benefit of compression from peripheral wheels 100 on both sides while the peripheral wheels 100 receive the benefit of compression from only one side. This imbalance causes the central wheel 101 to penetrate more deeply and is one of the central insights of the current invention disclosure.

Although not shown, the peripheral indenters may be coupled so they move together when moving reactively to the forces generated by the assembly pressing into the sample. This would obviate the need for one sensor—the center indenter and peripheral indenter pair may be each instrumented by one sensor for a total of two sensors.

Figure 28:
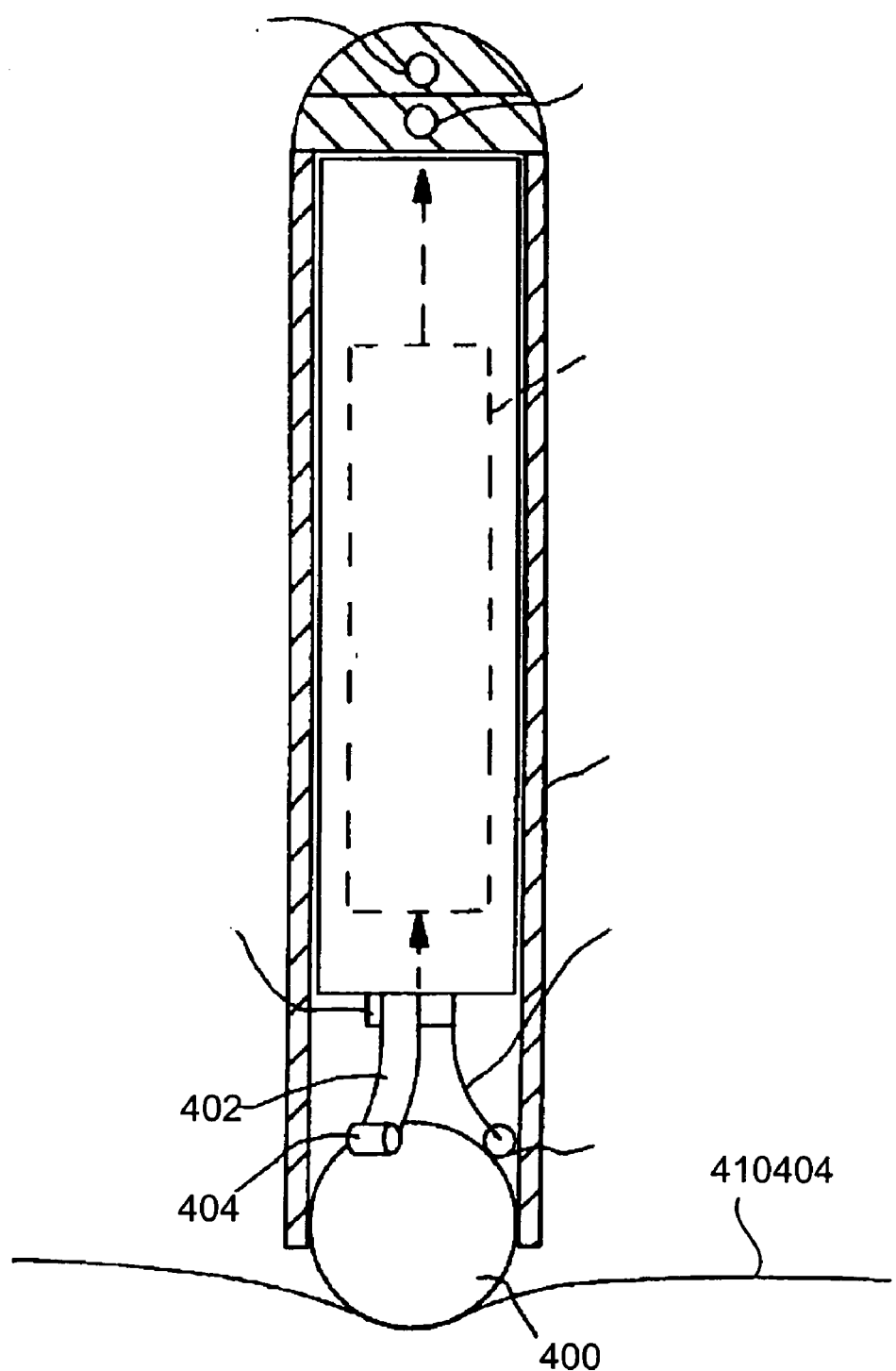
FIG. 28 is a view of Prior Art disclosed in Laird U.S. Pat. No. 5,833,634.
Figure 29:
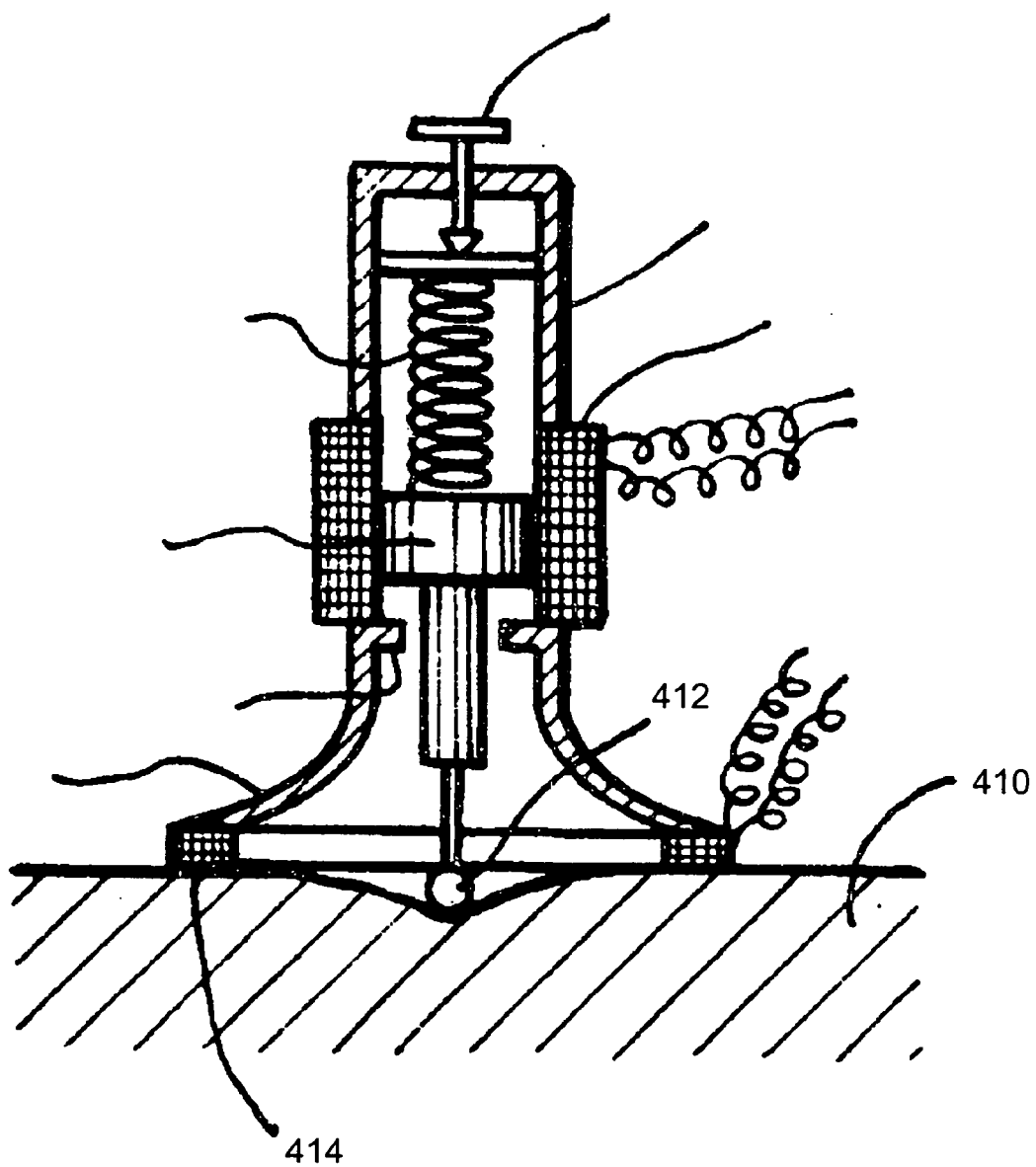
FIG. 29 is a view of Prior Art disclosed in Leveque U.S. Pat. No. 4,159,640.
Figure 30:
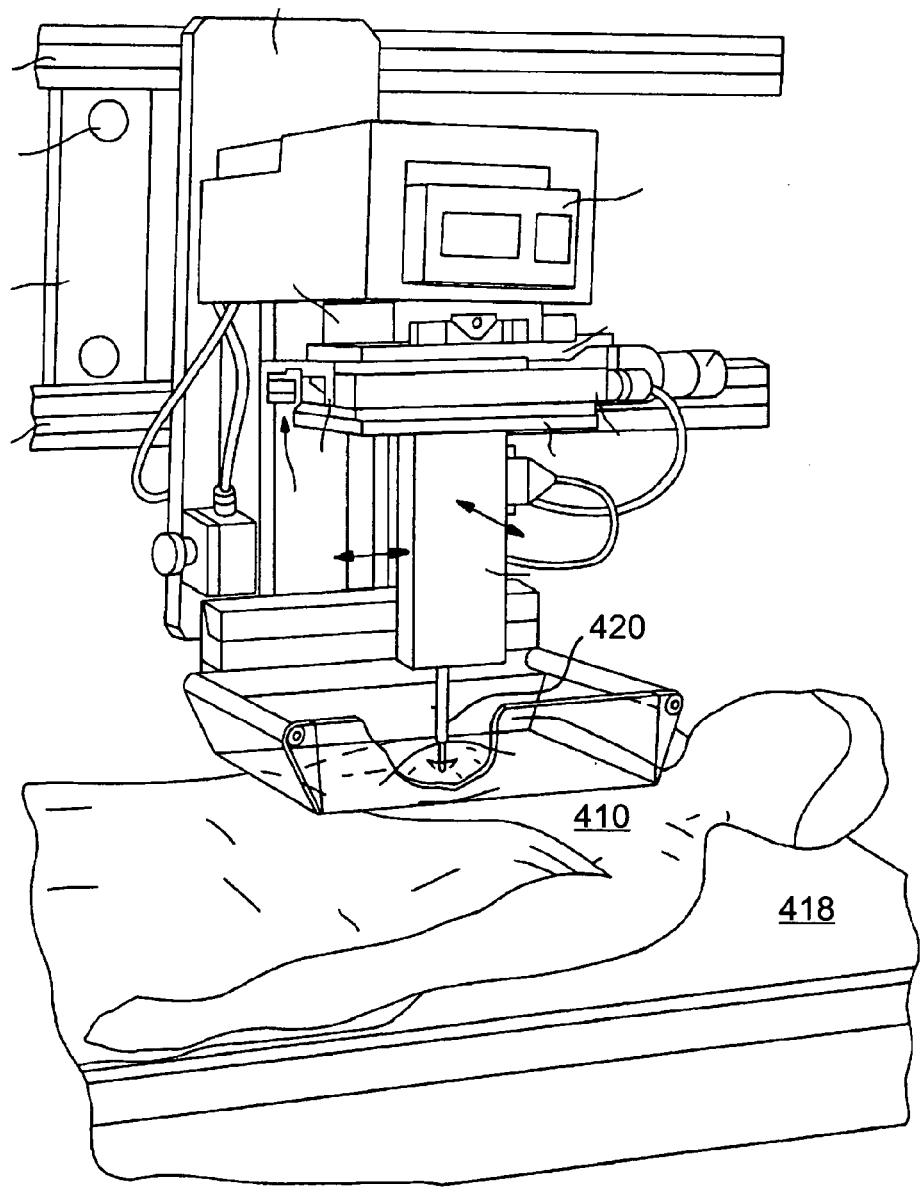
FIG. 30 is a view of Prior art disclosed in Lasky U.S. Pat. No. 6,190,334.
Figure 31:
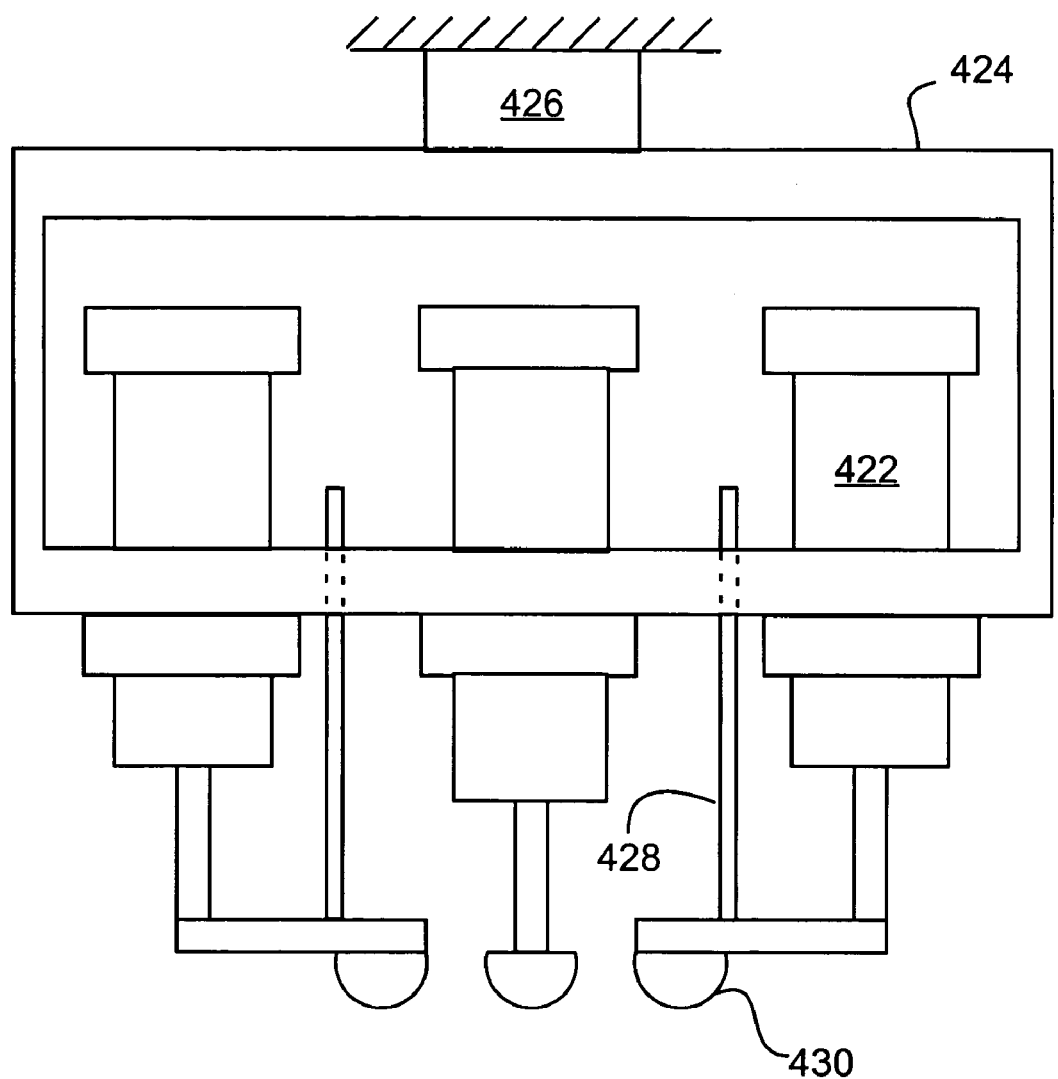
FIG. 31 is a view of Prior art disclosed in Ladeji-Osias, Ph.D. thesis, "The Biomechanics of Breast Palpation: Single and multi-probe indentation tests"

The Tri-Wheel implementation may be used to determine the firmness of a homogeneous sample or to detect gradients or boundaries of firmness within a sample (whether smooth or discontinuous). Prior art FIG. 28 attempts to locate such boundaries by measuring the direction of the reactive force vector but cannot be used to measure the firmness of a homogeneous sample.

Figure 22:
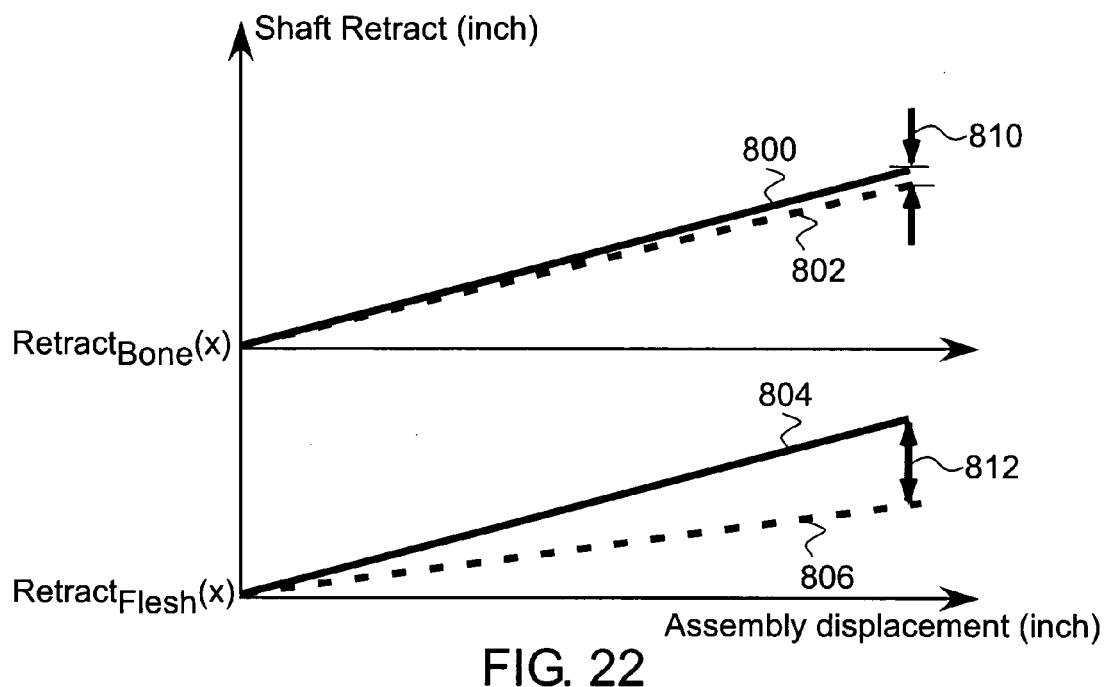
FIG. 22 is a graph showing four plots of displacement vs. displacement curves for the Tri-Wheel implementation (FIGS. 1 to 4)

FIG. 22 show the distance the spline shafts 108 and 109 retract into the fixture block 104 as the entire tri-wheel assembly 105 is pushed into the sample 121 (or vice versa). This retraction is proportional to the force exerted on that wheel by the sample 121 and is resisted by the springs 114. The bottom plot, RetractFlesh(x), shows the reaction of the tri-wheel assembly 105 as it is pushed into a fleshy 124 part of the sample 121. The upper plot, RetractBone, shows the reaction of the tri-wheel assembly 105 as it is pushed into a bony 122 part of the sample 121. Each plot consists of two traces. The dashed traces 806 and 802 show the retraction of the peripheral spline shaft when pushed into flesh 124 or bone 122, respectively. The solid traces 804 and 800 show the retraction of the peripheral spline shaft when pushed into flesh 124 or bone 122, respectively. Note that there are two peripheral shafts 108 and only one central shaft 109 so the traces representing the peripheral retraction 804 and 800 are representing two shafts each but since the assembly 105 is being pushed into a flat, locally homogeneous sample, they retract similar distances. These plots reveal that the difference in retraction between the central and peripheral shafts is greater when the assembly 105 is pushed into flesh 812 than when it is pushed into bone 810.

Figure 23:
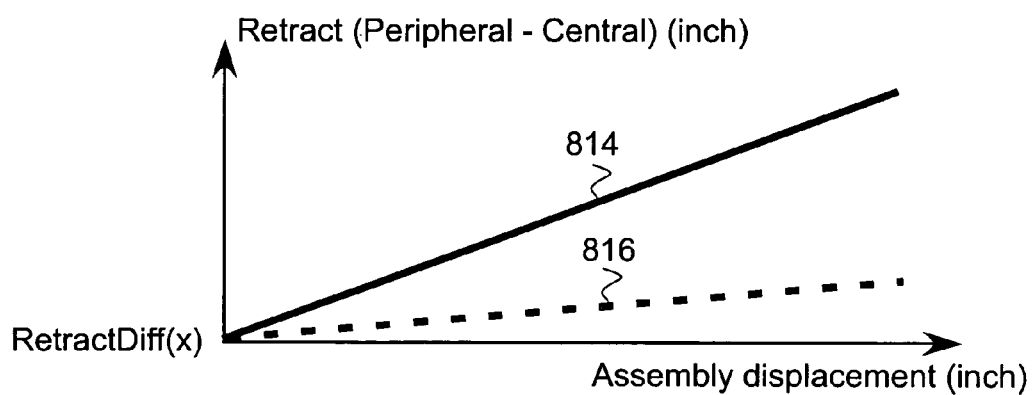
FIG. 23 is a graph reducing the four plots of FIG. 22 to two plots by showing the difference in compression displacement of the peripheral and central rollers when the Tri-Wheel implementation is pressed into flesh (814) and area of superficial bone (816)

FIG. 23 simplifies this relationship by showing the difference between peripheral shaft 108 retraction and central shaft 109 retraction plotted vs. assembly displacement as Tri-Wheel assembly 105 is pushed into test sample 121. This plot consists of two traces, 814 shows the difference when the assembly 105 is pushed into flesh 124 while 816 shows the difference when the assembly 105 is pushed into bone 122. Thus, for a given assembly displacement one can determine sample 121 firmness by measuring the slope of the difference between the retraction of the peripheral shafts 108 and the central shaft 109 into the fixture block 104. If this slope is steep as for 814, the sample 121 is likely soft flesh 124. If the slope is shallow as for 816, the sample 121 is likely hard bone 122.

Figure 24:
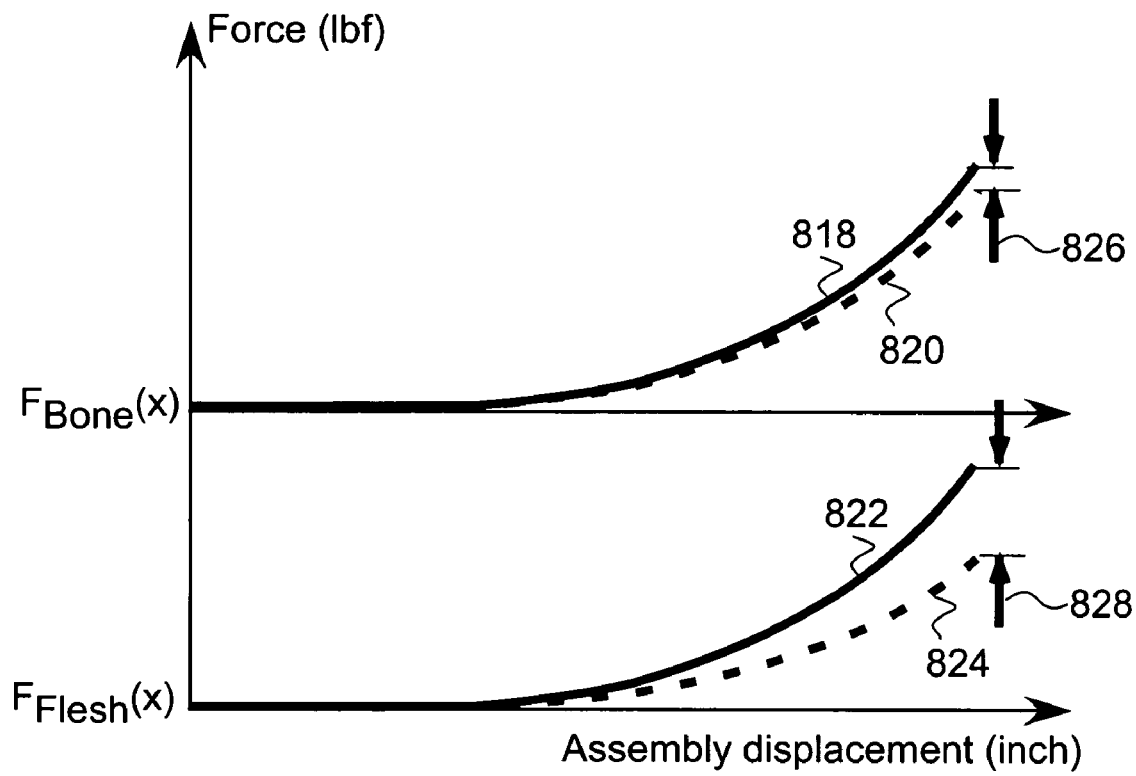
FIG. 24 is a graph showing four plots of force vs. displacement curves for the Tri-Wheel implementation (FIGS. 1 to 4)

FIG. 24 shows how the pervious measurement can be accomplished by measuring forces with the force-sensing sensors 102 instead of displacements which were measured above using the encoders 110 and 111 and encoder strips 118 and 119. In this figure, the bottom plot, FFlesh(x) has two traces. 822 shows the forces on the peripheral rollers 100 as the assembly 105 is pushed into flesh 124. 824 shows the forces on the central roller 101 as the assembly 105 is pushed into flesh 124. 818 shows the forces on the peripheral rollers 100 as the assembly 105 is pushed into bone 122. 820 shows the forces on the central roller 101 as the assembly 105 is pushed into bone 122.

Figure 25:
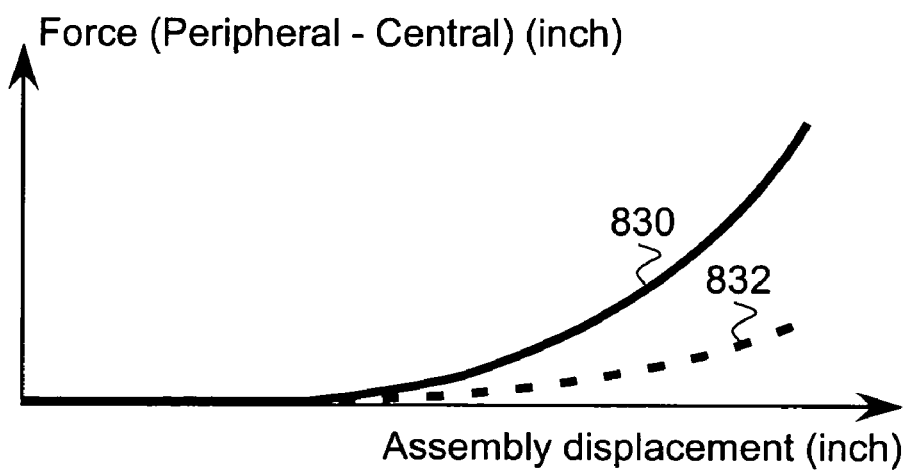
FIG. 25 is a graph reducing the four plots of FIG. 24 to two plots by showing the difference in force between the peripheral and central rollers when the Tri-Wheel implementation is pressed into flesh (830) and area of superficial bone (832)
Figure 26:
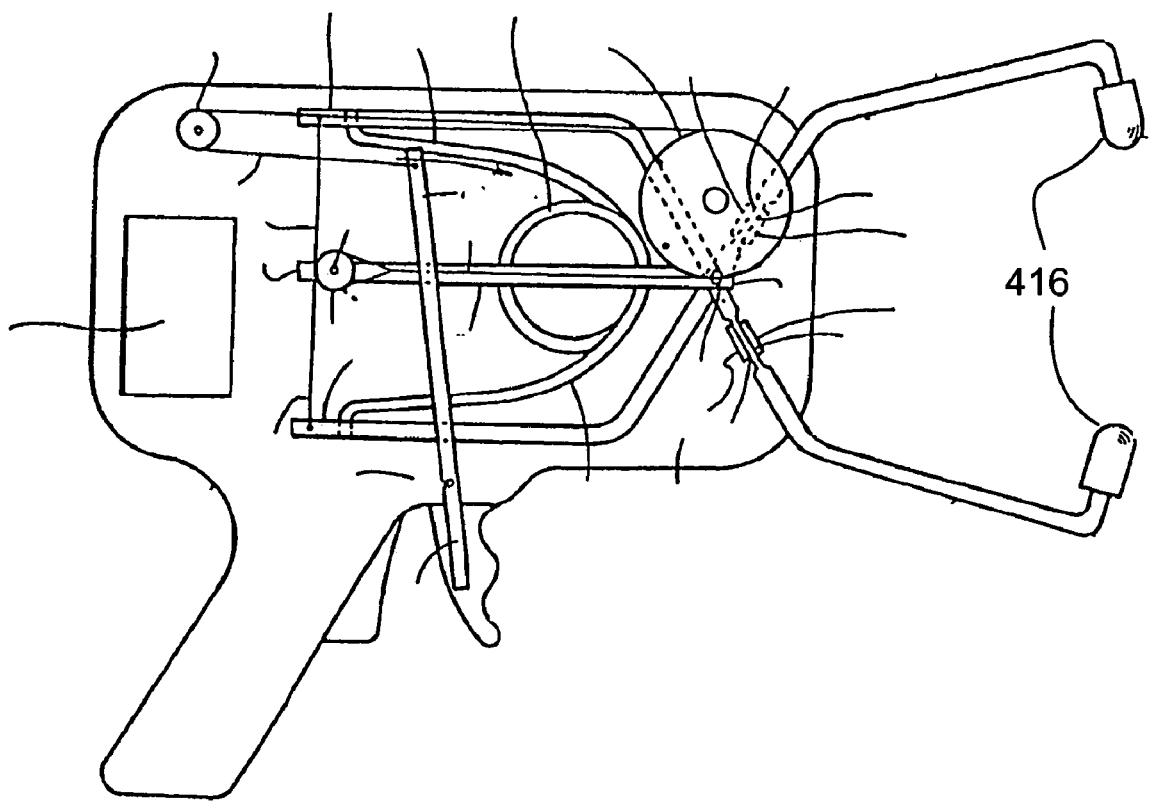
FIG. 26 is a view of Prior Art disclosed in Roush U.S. Pat. No. 5,038,795.
Figure 27:
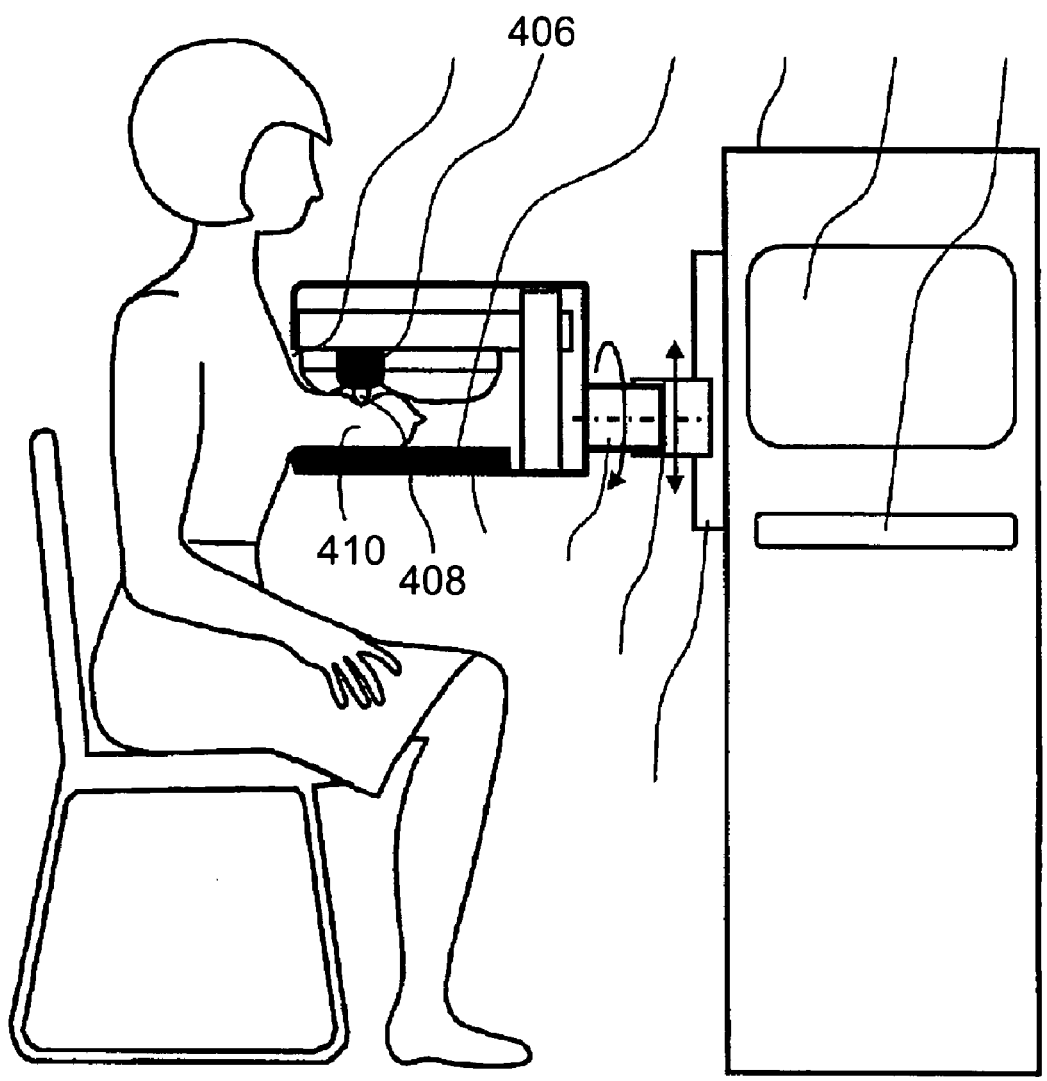
FIG. 27 is a view of Prior Art disclosed in Sarvazyan U.S. Pat. Nos. 5,524,636 and 5,833,633.

FIG. 25 shows the difference between the forces on the peripheral 100 and central 101 rollers as the assembly 105 is pushed into flesh 830 or bone 832. Compare this to FIG. 23 and it is clear that a controller could determine the firmness of a sample 121 using either the difference in force or in retraction distance.

Figure 34:
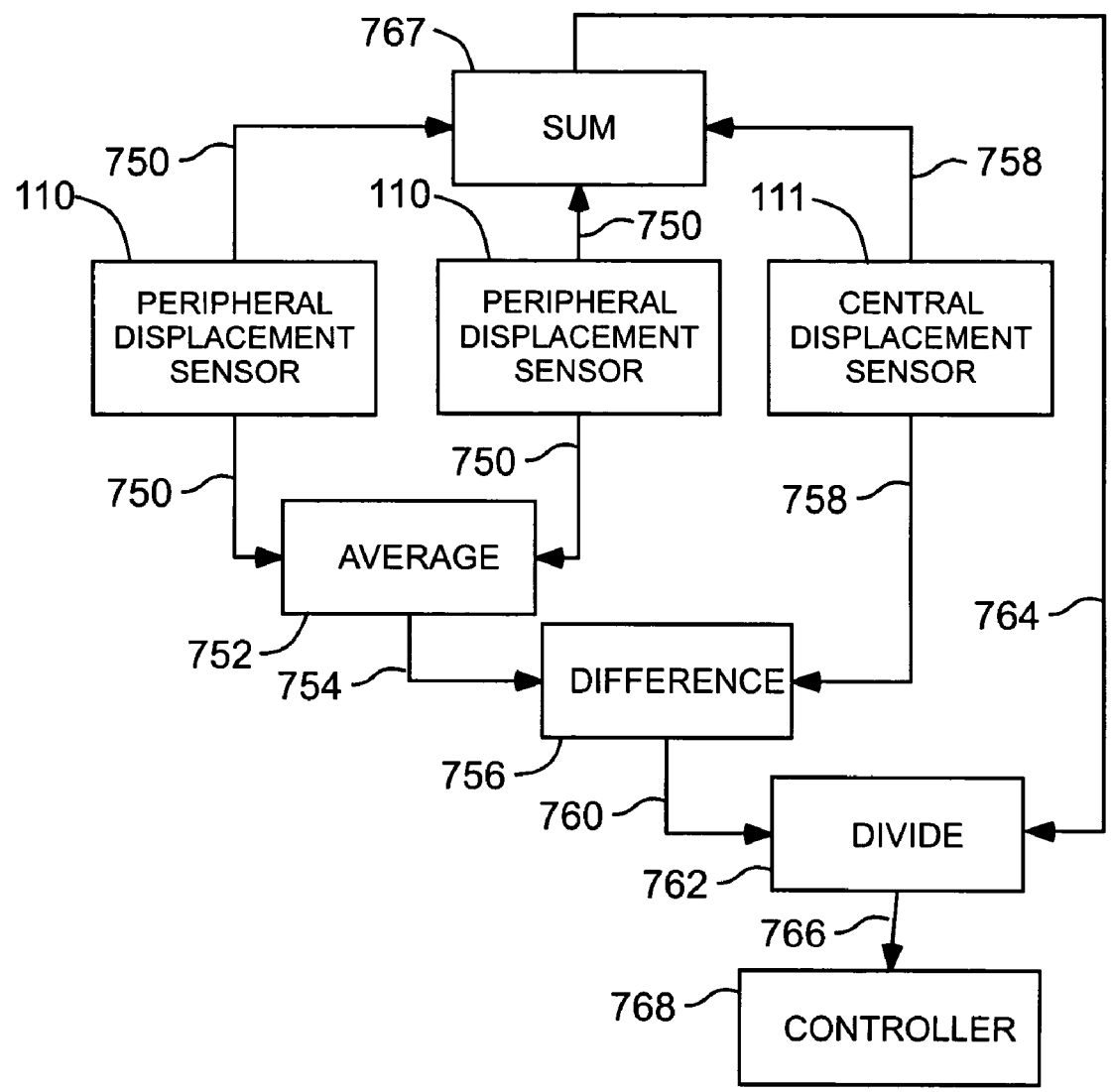
FIG. 34 is a data flowchart for Tri-Wheel, Thick Maze Wheel, and Thin Maze Wheel implementations of the present invention using linear displacement sensors to measure firmness of a sample.

FIG. 34 shows a flow chart representative of the encoder method and algorithm for analysis of information obtained by pressing the Tri-Wheel assembly 105 into a test subject sample 121. This method ignores the force sensing data and relies exclusively on the retraction encoders 110 and 111. In this method, the peripheral shafts 110 encoder positions 750 are averaged 752 and the result 754 is differenced 756 with the central shaft 111 encoder position 758. The shaft encoder positions 750 and 758 are also summed 767 and the sum 764 is then divided 762 by the difference result 760 to form a ratio 766 which is passed to the controller 768. The controller can then compare the ratio 766 to calibration data to determine the firmness of the test subject sample 121.

Figure 35:
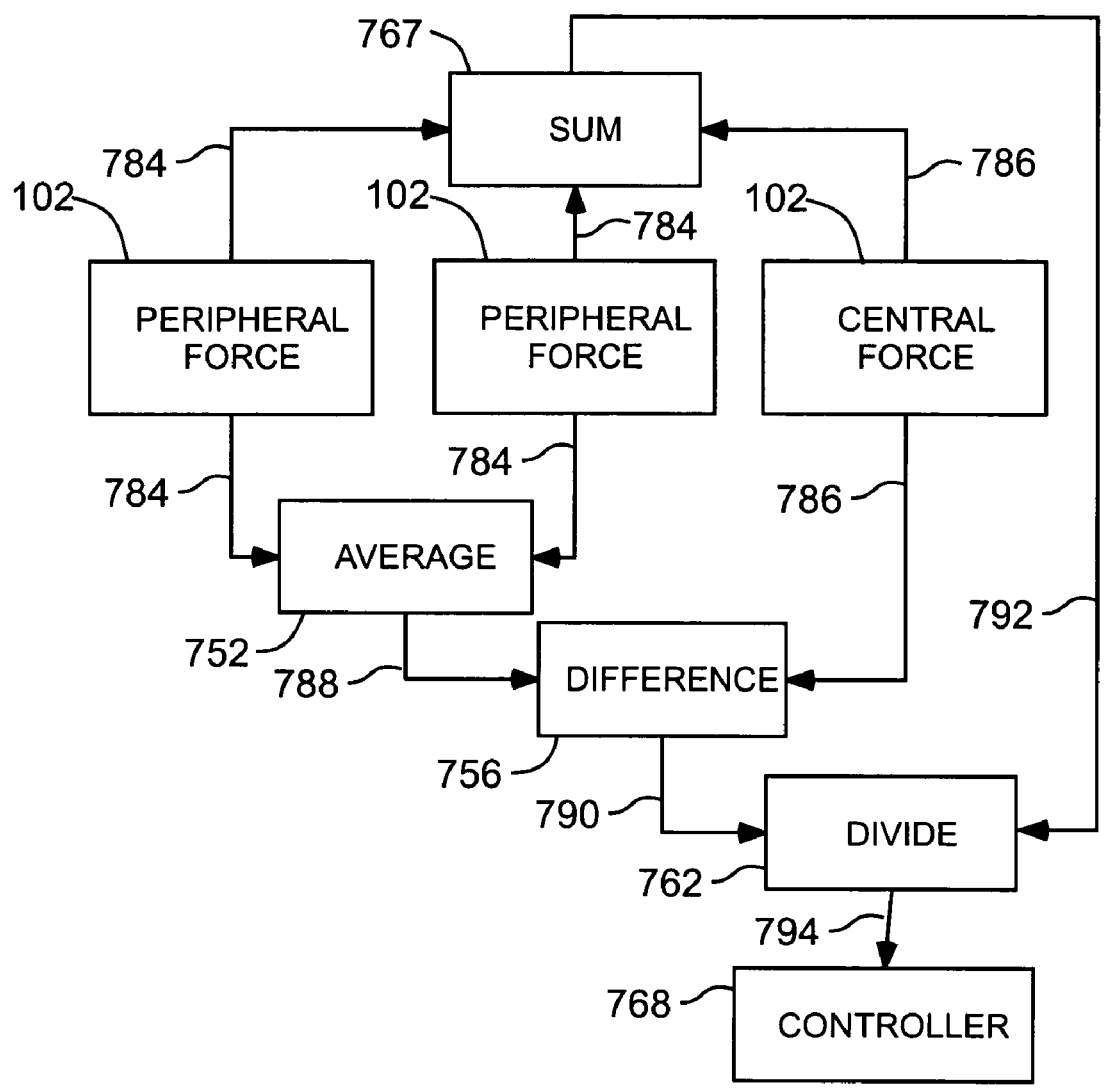
FIG. 35 is a data flowchart for the Tri-Wheel or Tread Wheel implementations of the present invention using force sensors to measure firmness of a sample.

FIG. 35 shows a flow chart representative of the force sensing method. This method is analogous to the encoder method depicted in FIG. 34 but uses force measurements instead of encoder measurements. In this method, the force data 784 from the force sensors 102 beneath the peripheral shafts 108 are averaged 752 and the result 788 is differenced 756 with the central shaft 109 force data 786. The forces for all three shafts 784 and 786 are also summed 767 and the sum 792 is then divided 762 by the difference result 790 to form a ratio 794 which is passed to the controller 768. The controller can then compare the ratio 766 to calibration data to determine the firmness of the test subject sample 121.

Note that the functions in FIGS. 34 and 35 specified by elements 752, 756, 762, and 766 may be separate from the controller 768 or they may be functions running within the controller 768. FIGS. 34 and 35 explain two preferred method but the controller may use the data emerging from the shaft encoders 110 and 111 and force sensors 102 differently from this method and arrive at similarly useful results. The algorithms described in FIGS. 34 and 35 may be combined, making use of both force and encoder data to provide additional insight, greater accuracy, or confirm the results provided by either of these algorithms used by itself.

The flow charts in FIGS. 34 and 35 also ignore the assembly 105 movement towards or away from the test subject sample 121 which may be available if, for example, the tri-wheel assembly 105 is moved by an XYZ motion platform in a massage chair such as that described in FIGS. 19 and 20. If this optional data were available, it may provide additional insight, greater accuracy, or confirm the results provided by the aforementioned algorithms. If such an XYZ motion platform is available, the controller 768 may make use of the firmness data measured in FIGS. 34 and 35 to avoid massaging too close to boundaries between bones 122 and flesh 124 which would otherwise cause the test subject 501 discomfort. The tri-wheel assembly 105 may be capable of differentiating between tense and relaxed flesh 124 in which case, the controller 768 may choose to concentrate on tense flesh.

The diameter and width of the wheels 100 and 101 depend on the scale of the firmness features in the sample 121 to be measured. These features may consist of bones 122 embedded in the flesh 124 or knots of muscle within the flesh 124. Additional rollers 100 may be provided above the three shown in FIGS. 1-4. For example, five such rollers 100 may be used to smooth the transitions between rollers 100 felt by the user.

In this embodiment, both force and displacement sensors are provided. In many cases, these will produce redundant data and only one or the other type of sensor is required. Force and displacement are generally related to each other. For example, if a spring loaded shaft is pushed into a sample and the spring compresses one inch, one may deduce the force on the shaft by knowing the spring constant of the spring. For example, the sprung shafts 108 and 109 paired with encoders 110 and 111 are capable of measuring the forces exerted on the wheels 100 and 101 without the force sensors 102 provided the system is calibrated to determine the force-displacement function of the system. This function encompasses the spring constant of the springs 114 as well as the weight, inertia, and friction of the rest of the system. Alternatively, if one doesn't know a priori how far the spring compressed but one does know from a force sensor that ten pounds are pressing upon the shaft, one can deduce the compression displacement of the spring, again by knowing the force-displacement function of the system.

A force sensor and a displacement sensor can be indistinguishable in certain circumstances. For example, a load cell measures the displacement of a physical structure with a known spring constant and returns a signal proportional to the force. Is a load cell a force or displacement sensor? The answer depends on how one chooses to interpret the data. A general feature of force sensors is that they are stiff while displacement sensors are relatively soft or may have no restraining force. For example, typical force sensors such as those specified as 102 in FIG. 2 compress a negligible distance before reaching their rated force. The sprung shafts 108 and 109 move significant distances before reaching maximum spring compressions.

Figure 5:
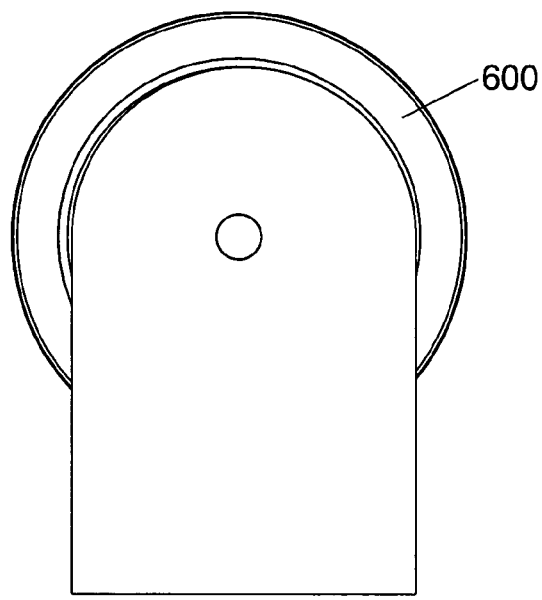
FIG. 5 is an orthogonal view of a Tread Wheel implementation according to the present invention showing the side of a wheel and bracket.
Figure 6:
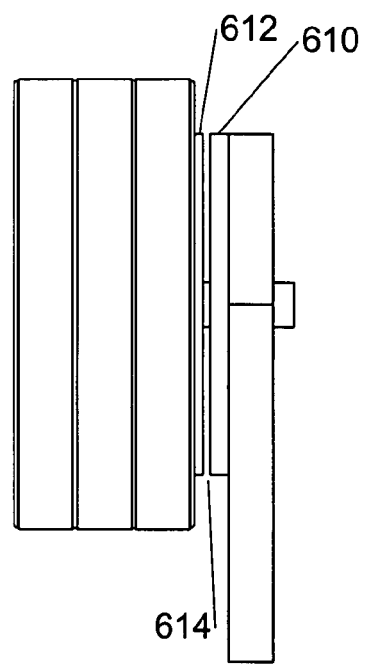
FIG. 6 is an orthogonal view of the Tread Wheel implementation of FIG. 5 showing a rolling surface of the wheel.
Figure 7:
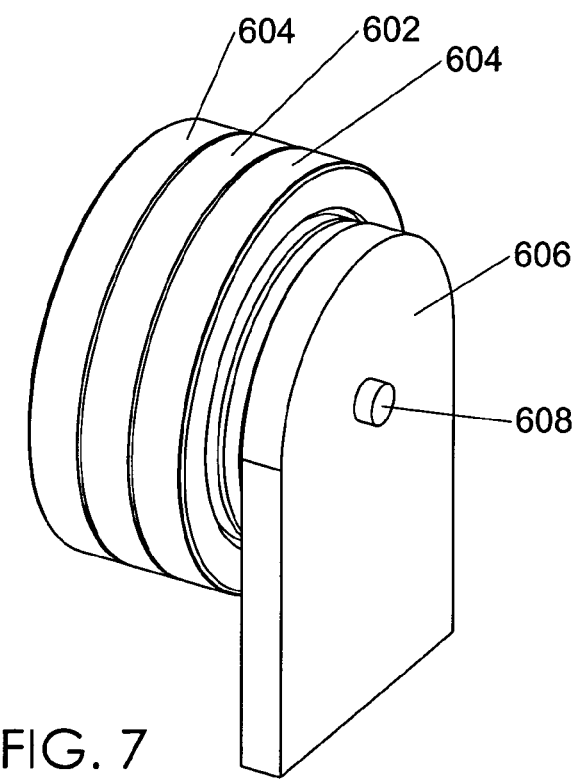
FIG. 7 is an isometric view of the Tread Wheel implementation of FIGS. 5 and 6 from the bracket side.
Figure 8:
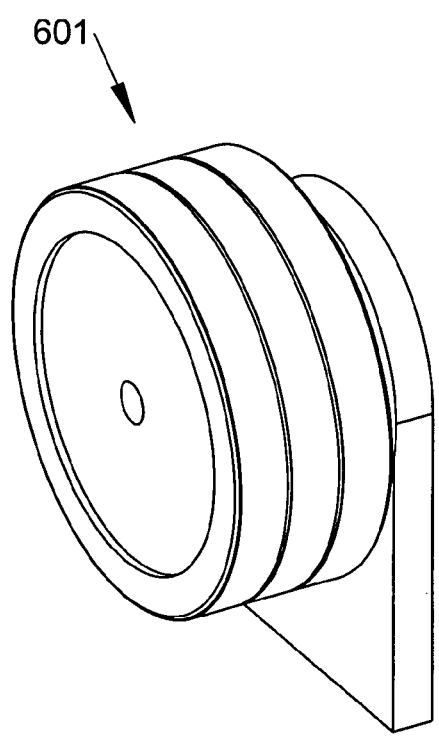
FIG. 8 is an isometric view of the Tread Wheel implementation of FIGS. 5 to 7 from the wheel side.
Figure 9:
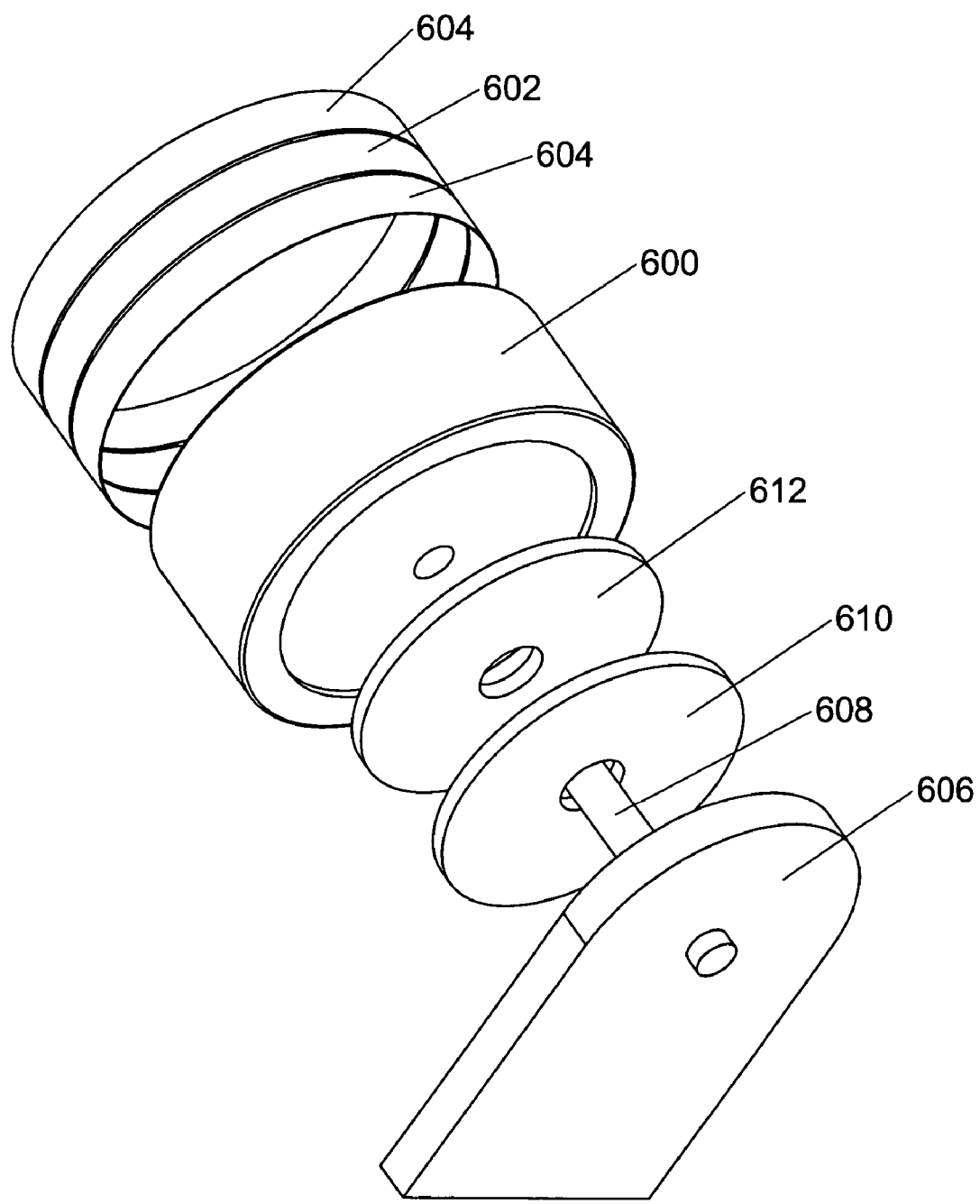
FIG. 9 is an exploded view of the Tread Wheel implementation of FIGS. 5 to 8.
Figure 10:
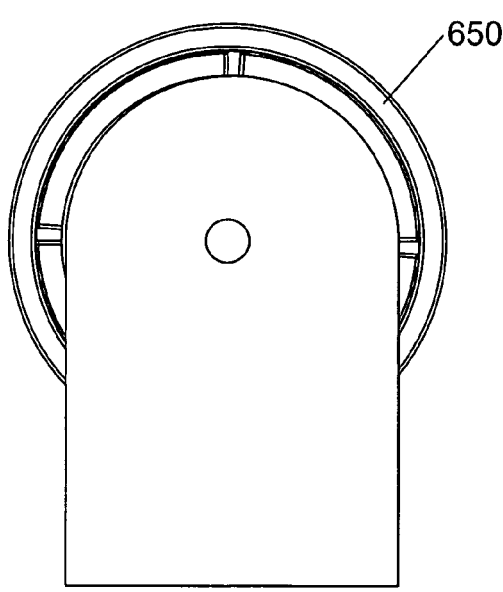
FIG. 10 is an orthogonal view of a Bending Wheel implementation according to the present invention showing the side of a wheel and bracket.
Figure 11:
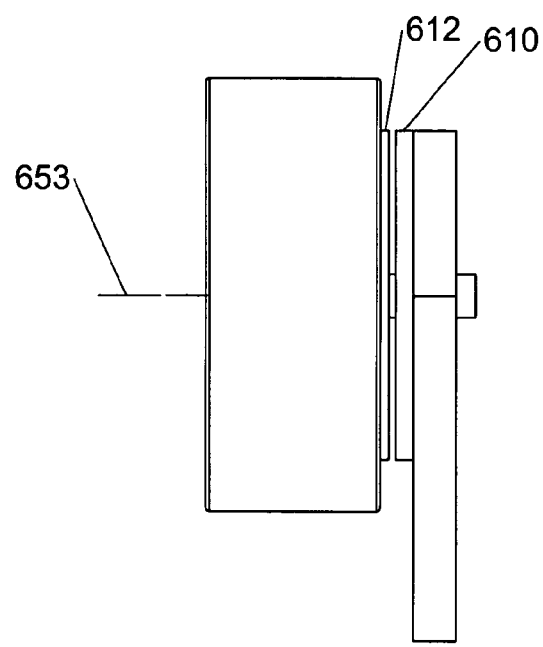
FIG. 11 is an orthogonal view of the Bending Wheel implementation of FIG. 10 showing a rolling surface of the wheel.
Figure 12:
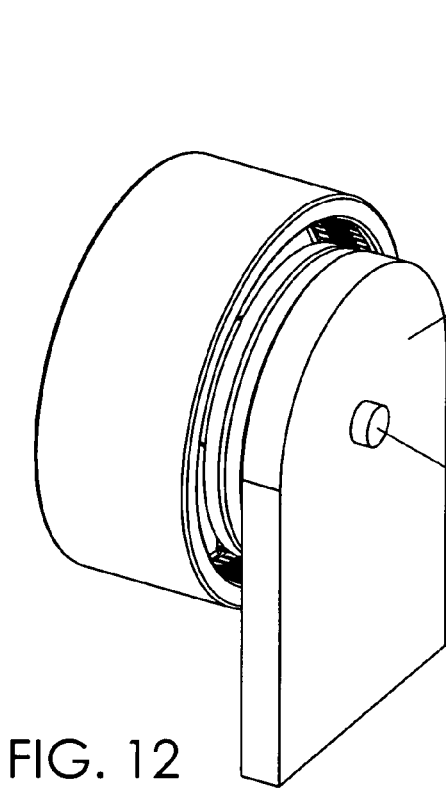
FIG. 12 is an isometric view of the Bending Wheel implementation of FIGS. 10 and 11 from the bracket side.
Figure 13:
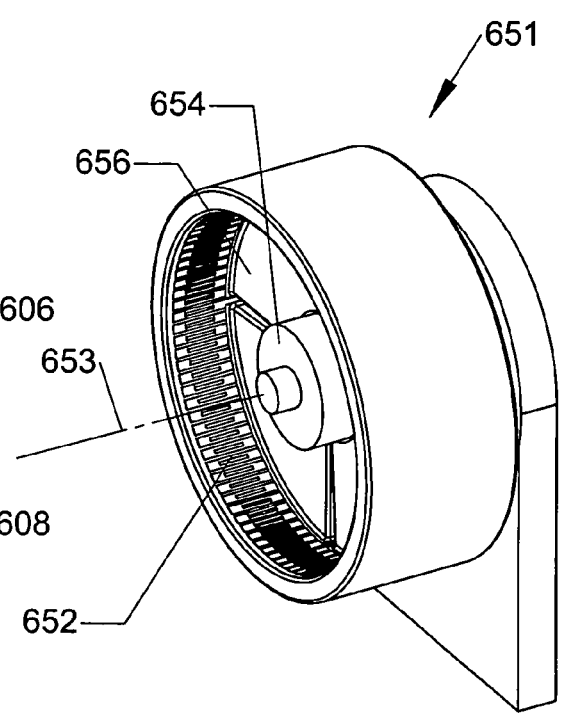
FIG. 13 is an orthogonal view of the Bending Wheel implementation of FIGS. 10 to 12 from the wheel side.
Figure 14:
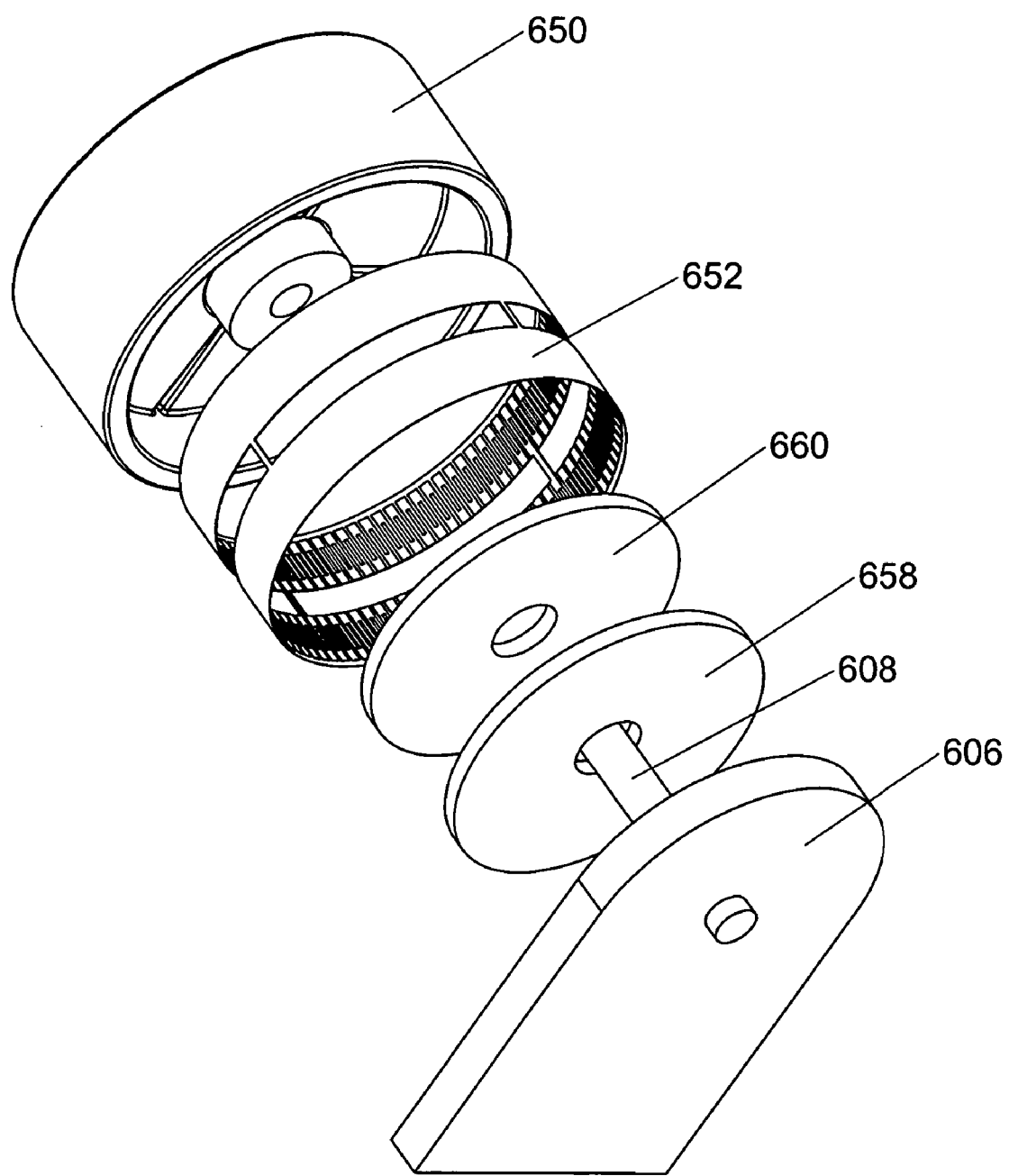
FIG. 14 is an exploded view of the Bending Wheel implementation of FIGS. 10 to 13.

FIGS. 5- to 9 show a "Tread Wheel" embodiment of the current application. This Tread Wheel assembly 601 consists of a single wheel 600 revolving on a shaft 608 which is mounted to a bracket 606 which would be mounted to some external device depending on the application. For example, this assembly may be mounted to an XYZ motion platform in a massage chair such as that described in FIGS. 19 and 20.

Mounted on the surface of the wheel 600 are three bands consisting of a central force sensing band 602 and two peripheral force sensing bands 604. Although not required, a favored configuration for these bands 602 and 604 is to be spaced with a minimal gap between them to minimize force transmitted from the sample 121 to the wheel 600 without being detected by the force sensing bands 602 and 604. For similar reasons, the peripheral force-sensing bands 604 may cover the wheel up to its edges. Though not required, the favored embodiment has the bands 602 and 604 of identical widths and the wheel 600 is flat across its surface.

The width of the force sensing bands 602 and 604 and the diameter and width of the wheel 600 depends on the scale of the firmness features in the sample 121 to be measured. These features may consist of bones 122 embedded in the flesh 124 or knots of muscle within the flesh.

The force sensing bands may be fabricated in a manner similar to those force sensors made by TekScan. They do not advertise a sensor which fits the shape required by the bands 602 and 604 described above but their technology can be straightforwardly adapted to produce force sensor in any desired configurations. Other technologies of force sensors may be used as their price makes them reasonable.

As the Tread Wheel assembly 601 is pushed into a flat rigid sample 121 such as the bone 122 as shown in FIG. 3, the peripheral 604 and central 602 bands will register similar forces. When the Tread Wheel assembly 601 is pushed into a flat softer sample 121 such as flesh 124 FIG. 4, the central band 602 will register a lower force than the peripheral bands 604. This is because the peripheral bands 604 compress the sample 121 on either side of the central band 602, reducing the restorative force of the flesh 124 trying to push back out. The central band 602 compresses the flesh 124 for the peripheral bands 604 but as in the tri-wheel embodiment, the central band 602 receives the benefit of compression of the flesh 124 from two sides while the peripheral bands 604 receive the benefit of compression of the flesh 124 from only one side. This imbalance causes the central band 602 to receive less restorative force from the sample 121 than the peripheral bands 604.

Depending on the desired feature geometry and firmness differences to be measured, this effect may be modified by recessing the central band 602 slightly into the wheel which will cause the peripheral bands 604 to absorb a larger fraction of the restorative forces. This redistribution of force from the central to peripheral bands is more pronounced when the sample 121 is bony 122 than when it is fleshy 124. A sample 121 which is fleshy 124 will conform more easily to the recessed central band 602 and so the forces on the central and peripheral bands will be more similar than if the sample 121 is bony 122. Alternatively, the central Band 602 may protrude from the wheel past the peripheral bands 604 which would cause the inverse effect. This would cause the assembly to feel more comfortable to the user which may be of overriding importance in some applications The flowchart FIG. 36, which was used to describe the Tri-Wheel configuration, also describes the algorithm and method to be used by the Tread Wheel configuration.

The Tread Wheel sensors are powered by electricity which is conveyed from the external assembly to the rotating wheel 600 by means of an inductive power and data coupling. The stationary coupling 610 generates an AC EMF waveform which couples into a transformer on the rotating coupling 612, which rectifies the signal to produce power. Similarly, the sensed force data may be digitized or left as analog and is converted to an AC waveform which is passed back from the rotating coupling 612 to the stationary coupling 610. An example of this type of coupling is made by Mesa Systems of Medfield, Mass. Brushed slip rings or other technologies may be used in lieu of the inductive couplings.

FIGS. 10 to 14 show a "Bending Wheel" embodiment. This Bending Wheel assembly 651 consists of a single wheel 650 revolving on a shaft 608 which is mounted to a bracket 606 which would be mounted to some external device depending on the application. For example, this assembly may be mounted to an XYZ motion platform in a massage chair such as that described in FIGS. 19 and 20.

Mounted on the inside surface of the wheel 650 are one or more strain gauges 652. Although not required, a favored configuration is for the wheel to have a hub 654 riding on the shaft 608 and connected to the wheel 650 via a stiffening disc 656. This figure shows the stiffening disc 656 connected to the wheel 650 at a circumferential seam along the midpoint of the inside of the wheel 650. This makes the wheel stiff along it's middle but deformable away from the stiffening disc 656.

Figure 37:
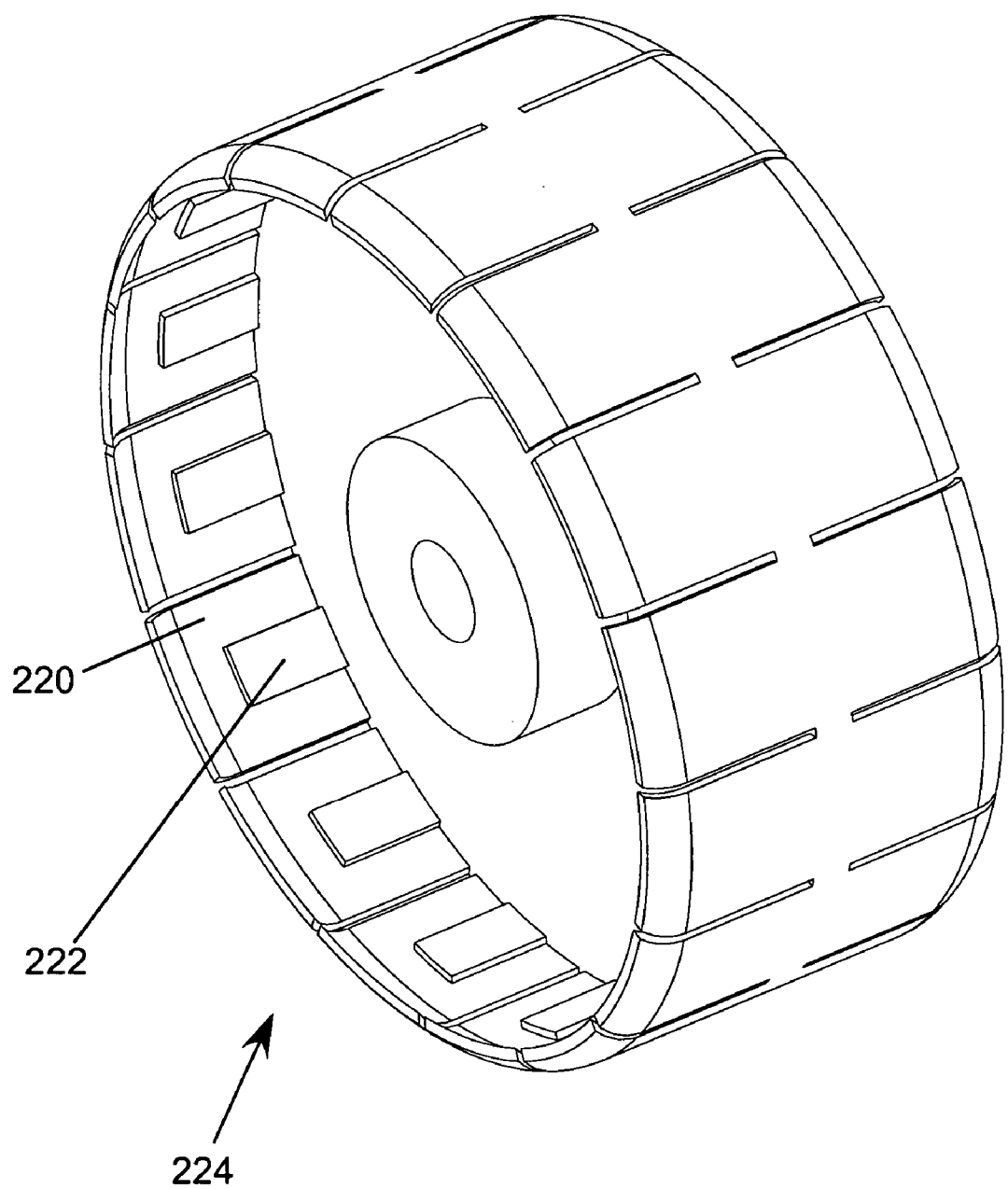
FIG. 37 is an isometric view of a Segmented Bending Wheel implementation according to the present invention.

There are many alternative configurations such as two stiffening discs 656 on the outside faces of the wheel 650 which causes the wheel tread 650 to be stiff on its periphery and soft along its center. The wheel 650 can be segmented to allow greater flexibility for the segments to flex towards the axel 608 when pressed into a soft sample. FIG. 37 shows such a Segmented Bending Wheel 224 with discrete strain gauges 222 on each segment 220.

Figure 32:
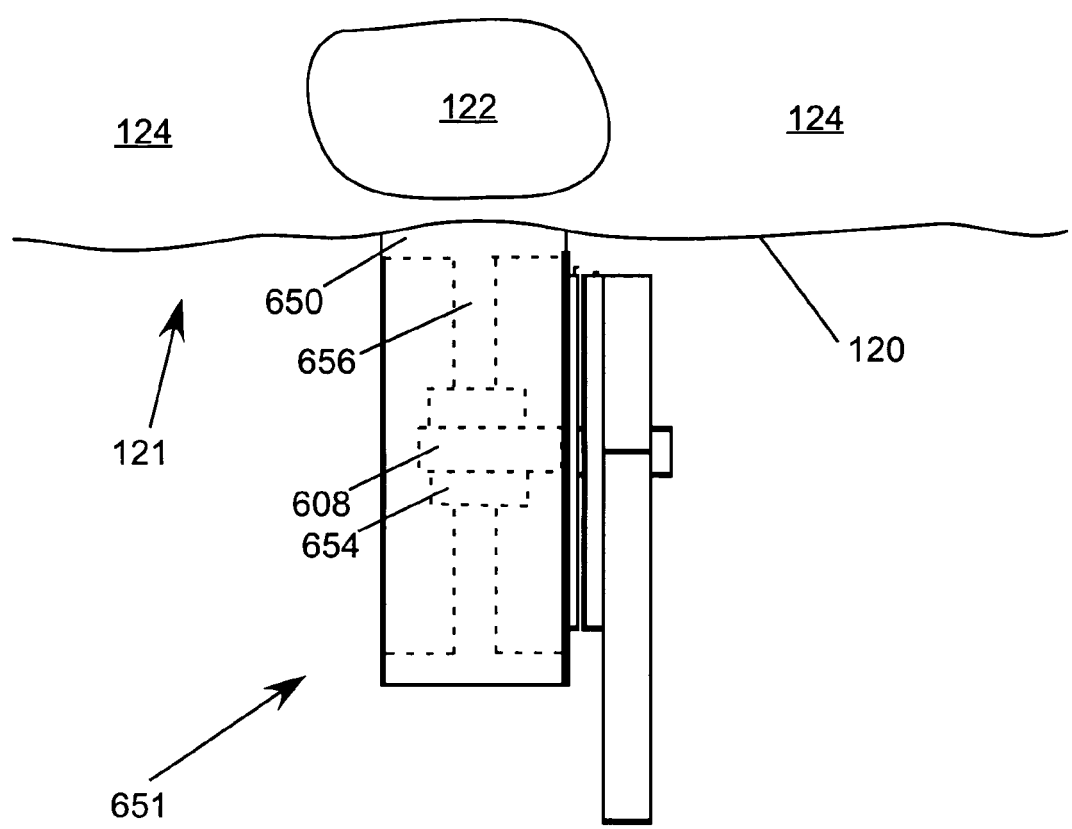
FIG. 32 is an orthogonal view of the Bending Wheel assembly of FIGS. 10 to 15 pressing into an area of the user with superficial bone.

As shown in FIG. 32, when the Bending Wheel assembly 651 is pressed into a hard, bony 122 part of a sample 121, the wheel 650 retains its original shape and most of the force is supported by the wheel 650 in the contact patch between the sample 121 and the stiffening disc 656. The rest of the contact patch does not sustain much contact force.

Figure 33:
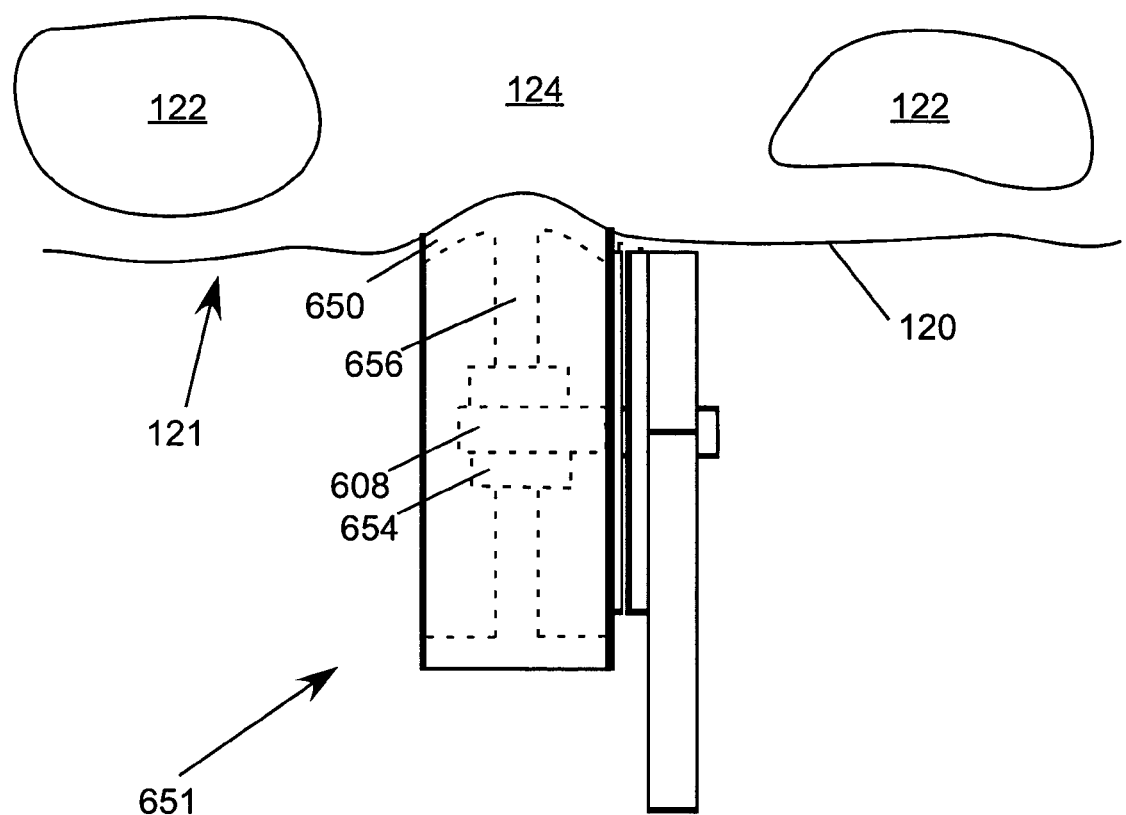
FIG. 33 is an orthogonal view of the Bending Wheel assembly FIGS. 10 to 15 pressing into a soft (fleshy) area.

As shown in FIG. 33, when the Bending Wheel assembly 651 is pressed into a soft fleshy 124 part of a sample 121, the wheel 650 bends backwards along the contact patch due to the reactive force of the sample 121 pressing back against the wheel 650. The wheel 650 is stiff near the stiffening disc 656 but is more free to bend backwards close to the edges of the wheel 650. The degree of this bending is related to the softness of the sample 121 and the force with which the Bending Wheel assembly 651 is pushed into the sample 121. The harder the sample 121, the less the wheel 650 will bend back.

The strain gauge 652 has its active grid length oriented along the axis of the roller 653 so that it can measure the degree of bending deformation across the width of the wheel. The wheel 650 diameter and width depend on the scale of the firmness features in the sample 121 to be measured. Power and data are transferred between the external assembly and the rotating wheel by a similar coupling 610 and 612 to that described in the Tread Wheel assembly 601 in FIGS. 5-9.

Figure 38:
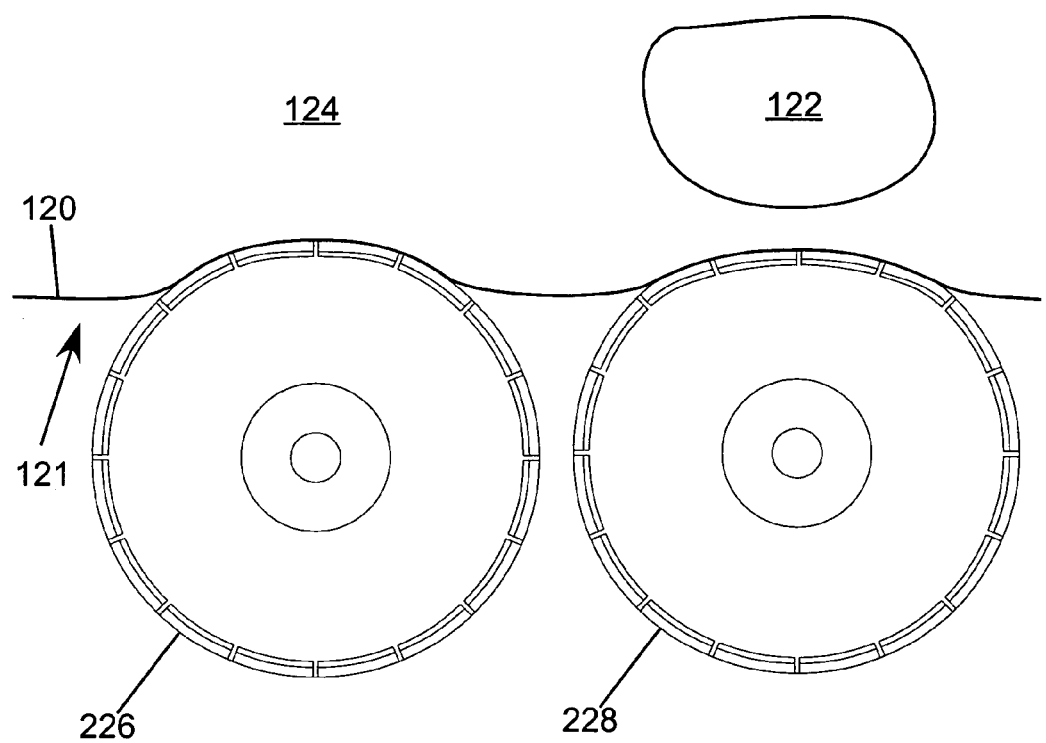
FIG. 38 is an orthogonal view of the Segmented Bending Wheel implementation of FIG. 37 pushed into soft and firm areas of a sample.

Alternatively, the wheel may be designed to deform into a flat contact area when pushed into a firm sample. FIG. 38 shows a segmented Bending Wheel 226 being pushed into sample 121 in a soft, fleshy area 124 such that the wheel deforms minimally. In another section of the sample, a segmented Bending Wheel 228 is pushed with the same force into an area of the sample 121 with a superficial bone 122 causing the segmented Bending Wheel 228 to deform with a larger, more pronounced flat area. This figure demonstrates that the deformation measurement means could be configured to measure deformation along the circumference of the wheel as opposed to across the width of the wheel.

Figure 36:
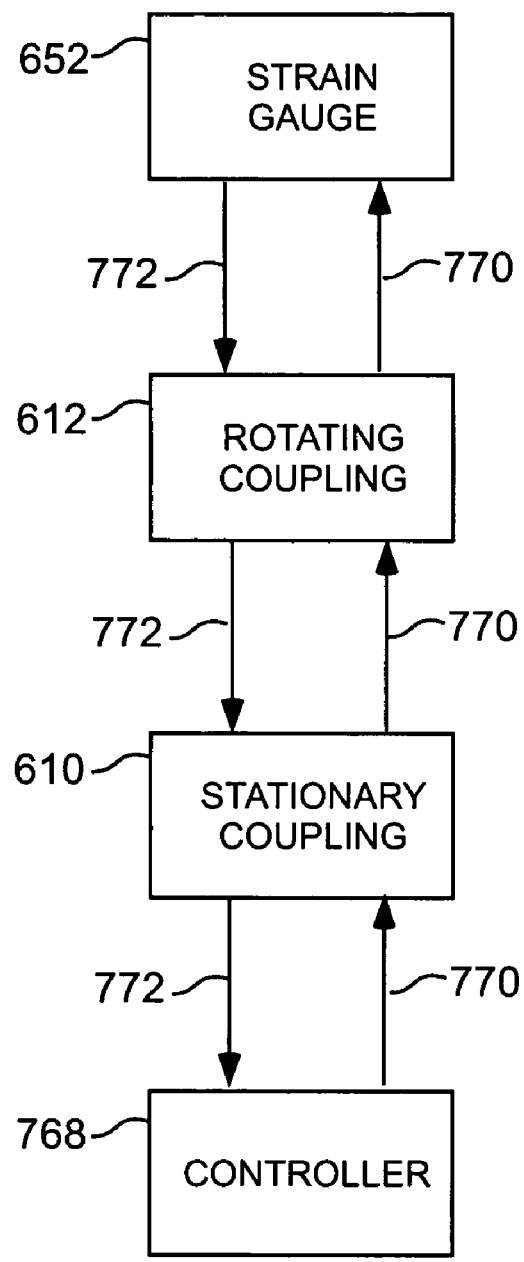
FIG. 36 is a data flowchart for the Bending Wheel implementation of the present invention using at least one strain gauge to measure firmness of a sample.

FIG. 36 shows the data flow for this embodiment. The controller 768 passes power 770 through stationary coupling 610 to the rotating coupling 612 which acts as the excitation voltage for the strain gauge 652. The strain gauge 652 produces an output signal 772 proportional to the bending strain which is passed back through the rotating 612 and stationary 610 coupling to the controller 768.

The strain gauge 652 may be configured with one output 772 or many. If the wheel 650 is covered with multiple strain gauges 652 with separate outputs 772, this may provide additional measurement accuracy but would require a controller 768 capable of determining which gauges 652 are "active" and should be used to calculate firmness. The depicted configuration shows a strain gauge 652 with a single output 772. Other technologies may be used instead of a strain gauge to measure the degree of wheel bending. For example a capacitive sensor could measure the distance between the wheel 650 flange tip and the stiffening disc 656.

Figure 39:
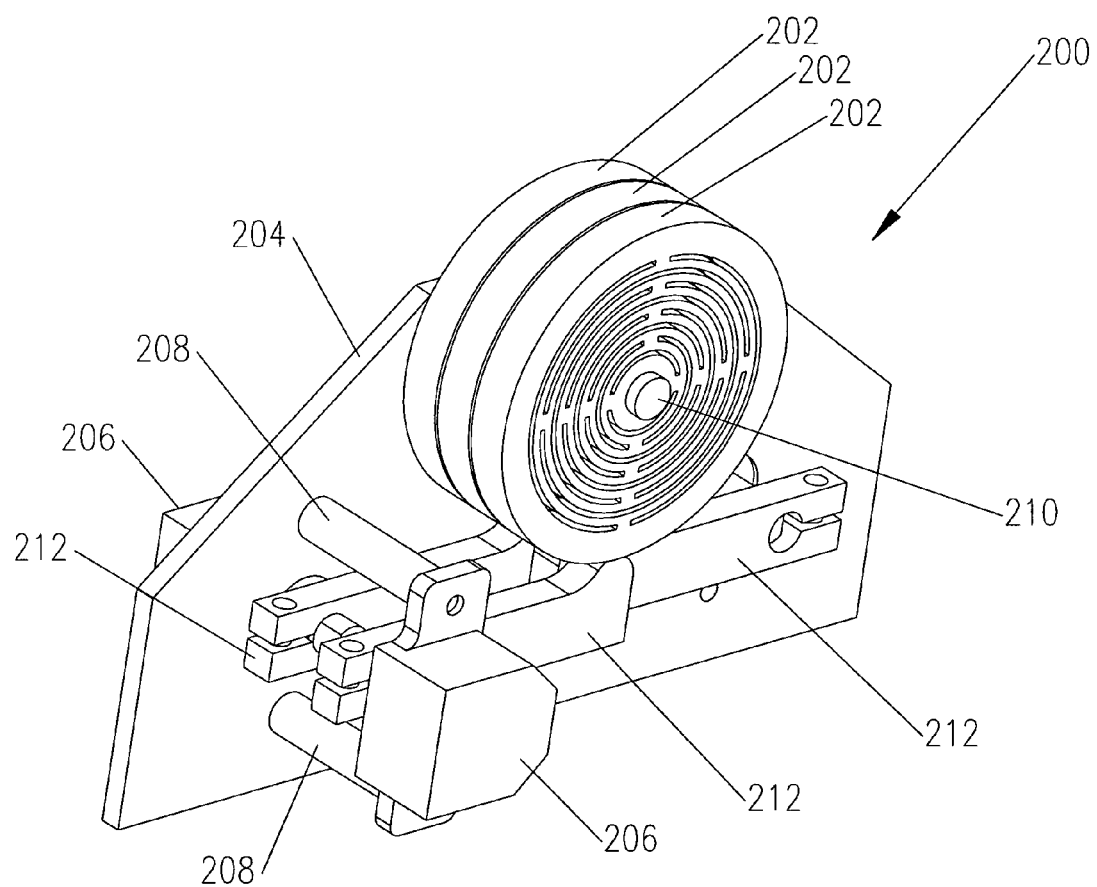
FIG. 39 is an isometric view of a Maze Wheel implementation of the present invention.
Figure 40:
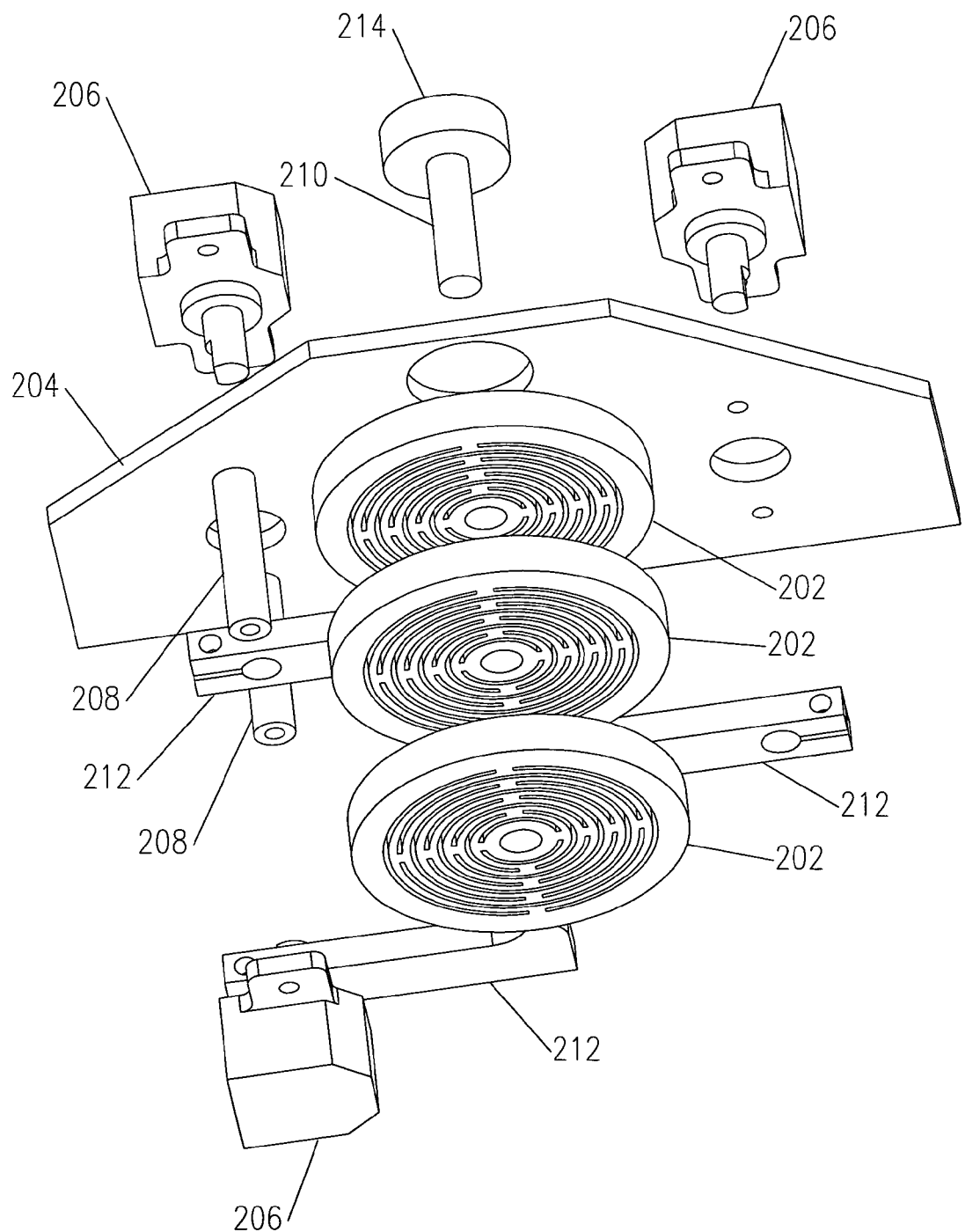
FIG. 40 is an exploded view of the Maze Wheel implementation of FIG. 39.

FIGS. 39 to 40 show a "Thick Maze Wheel" embodiment. This Thick Maze Wheel assembly 200 consists of three thick maze wheels 202 pressed onto a shaft 210 which is itself pressed into a bearing 214. The bearing is pressed into a mounting plate 204 which holds the three maze wheels 202 pressed against three spring-loaded followers 212 which actuate three rotary potentiometers 206 mounted through the mounting plate 204 or on standoffs 208.

The Thick Maze Wheel embodiment has the drawback that with a small number of relatively thick maze wheels 202, the discontinuity between adjacent maze wheels 202 when the assembly 200 is pushed into a user's back and the center maze wheel 202 protrudes farther into the user's flesh may cause discomfort as the edges of each wheel poke into the user. This drawback is shared by the Tri-Wheel embodiment. Both embodiments therefore recognize the possibility of adding additional wheels to provide a more continuously conforming surface.

FIGS. 41 to 48 show the "Thin Maze Wheel" embodiment. This thin maze wheel assembly 231 consists of 20 thin maze wheels 230 layered between twenty-one lubricious washers 232 and all mounted on a shaft 234 rotating on a pair of bearings 236. The bearings are mounted in a bracket 238 which supports three spring-driven LVDT linear position sensors 240 such as Sensotec's model PLVX-AY111HM LVDT.

Figure 43:
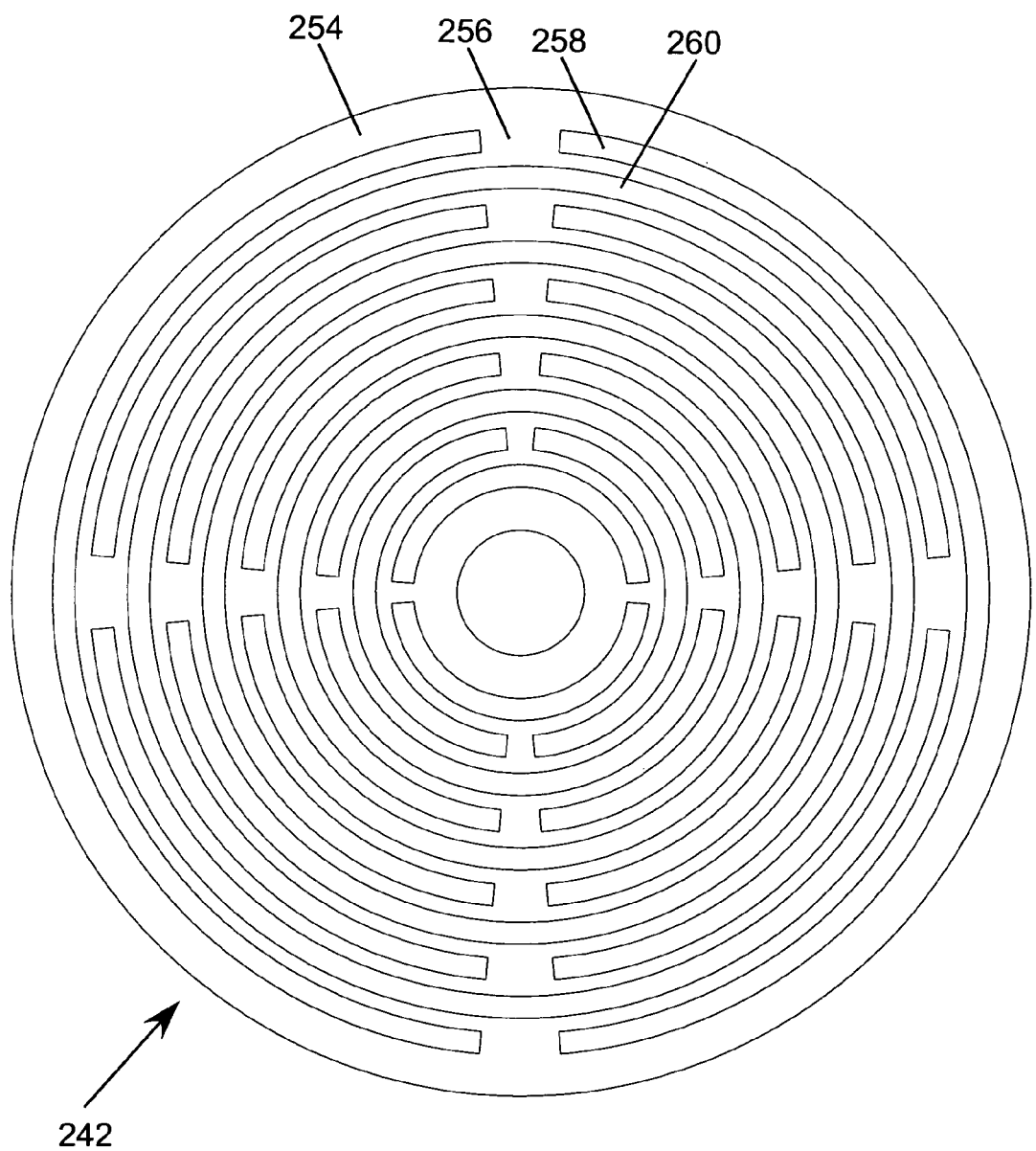
FIG. 43 is an orthogonal view of the Thin Maze Wheel of the assembly of FIGS. 41 and 42.

In the Thin Maze Wheel embodiments, force on the thin maze wheels 230 cause them to deform such that the outer annulus 254 shifts radially with respect to the shaft 234. As shown in FIG. 43, the thin maze wheel 242 is organized as pairs of concentric slots 258 spanning 170 degrees of the circle with supports 256 spanning 10 degrees each at each end of the slot 258. Each successive pair of slots is rotated 90 degrees relative to the next concentric slot neighbor 260.

Alternatively, the Maze Wheel may be fabricated as a disc of elastomeric material with an annulus of more rigid material. For example, the maze portion of the maze wheel 242 could be replaced with a rubber foam. A foam (with voids dispersed through the matrix) would allow the disc to deform without requiring empty space adjacent to the discs to absorb the bulging of the disc on the side closest to contact with the sample. These comments are meant to point out that although the favored implementation of the Maze Wheel embodiments describes a series of slots and deforming concentric cantilevers, there are other constructions to design such deformable wheels.

Figure 41:
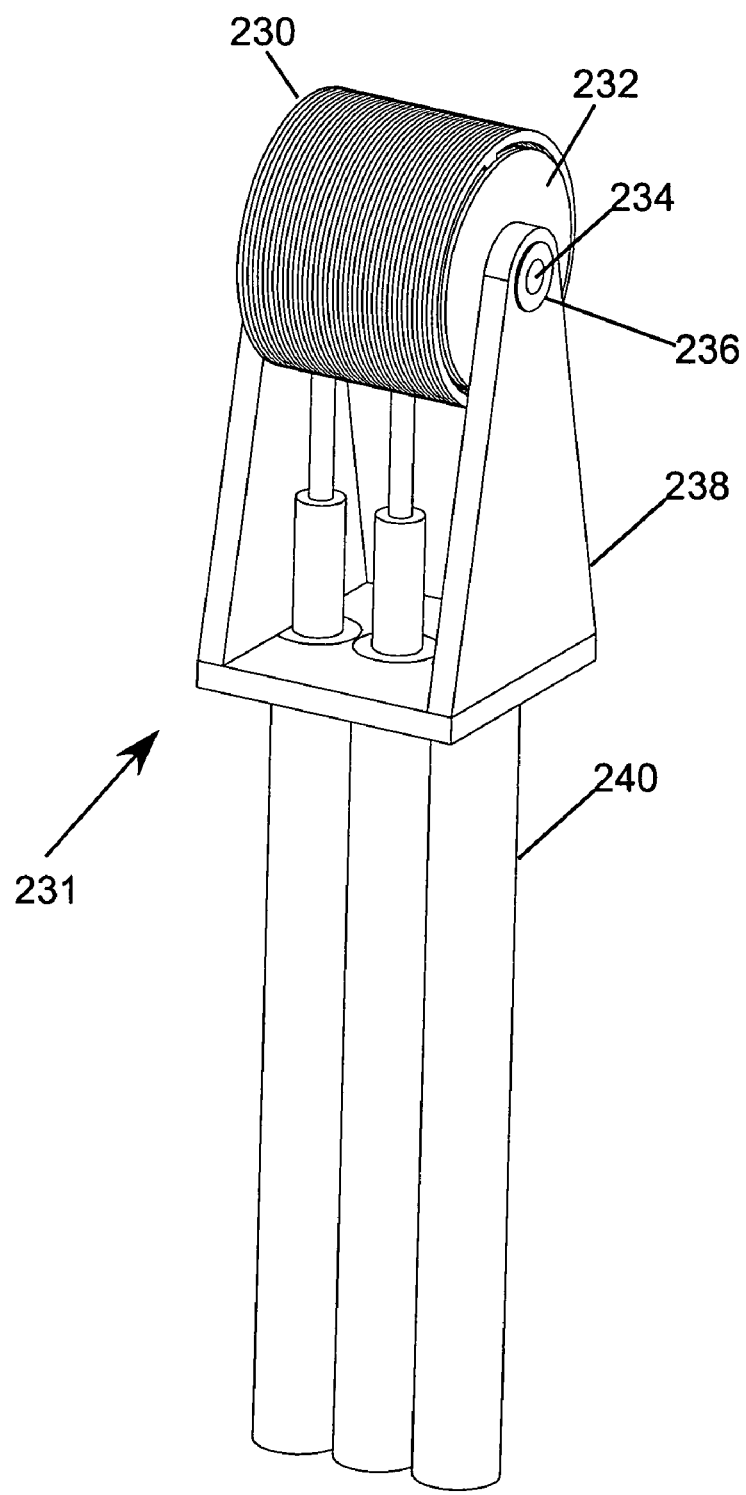
FIG. 41 is an isometric view of a Thin Maze Wheel assembly according to the present invention.
Figure 42:
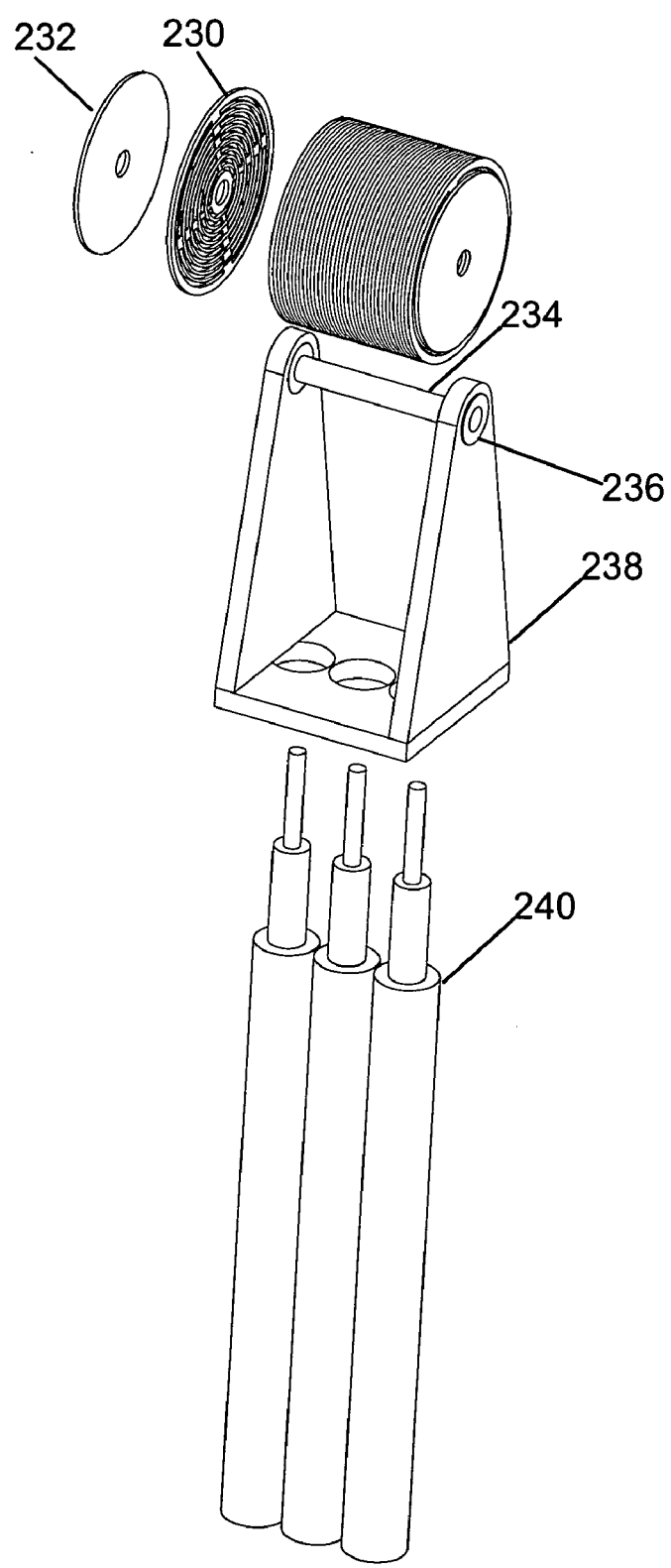
FIG. 42 is an exploded view of the Thin Maze Wheel assembly of FIG. 41.
Figure 44:
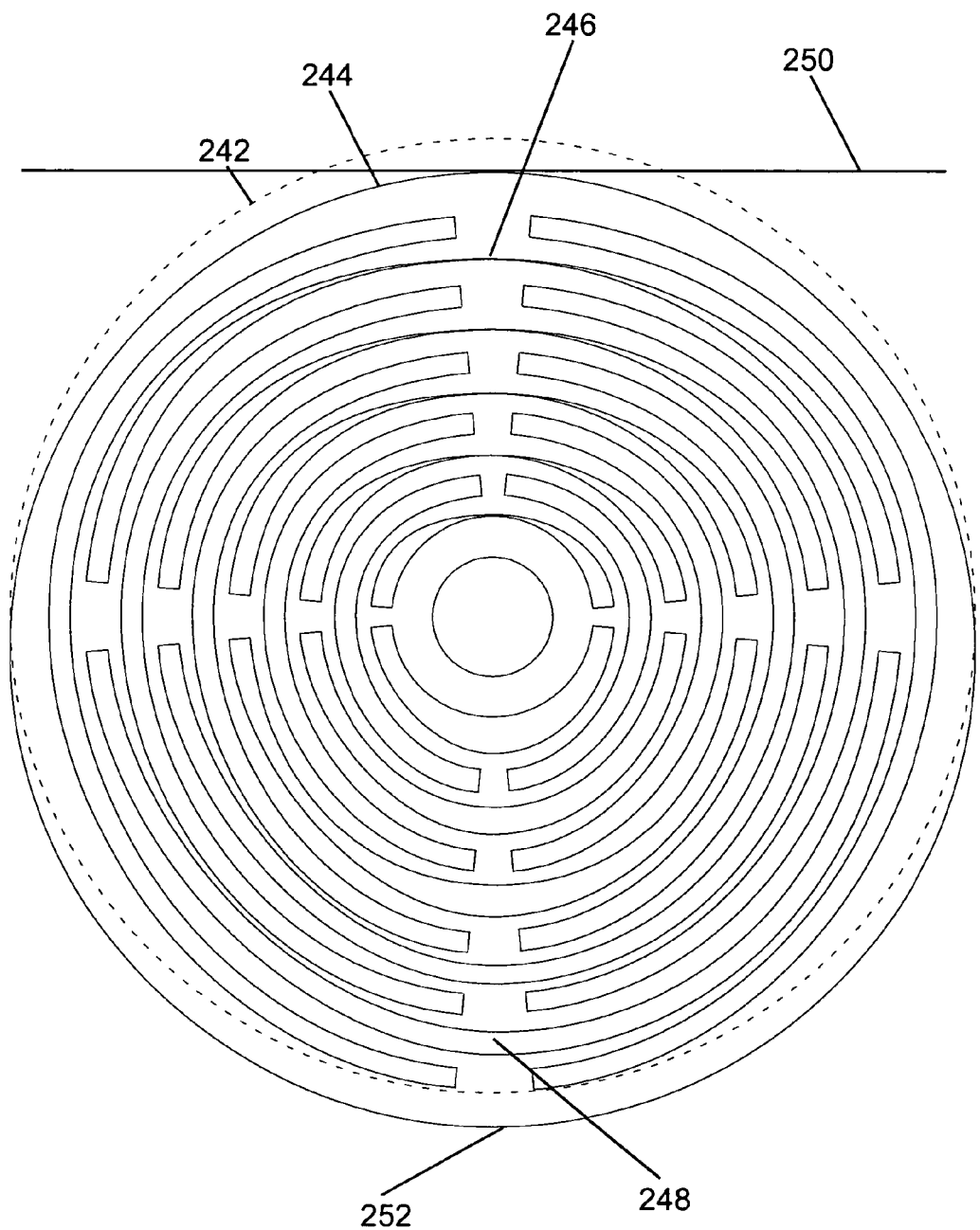
FIG. 44 is an orthogonal view showing deformation of the Thin Maze Wheel of FIG. 43.

FIG. 44 shows the deformation when thin maze wheel 242 is pressed into a hard surface 250. This causes half of the slots to be deformed when, as shown, the force applied by the hard surface 250 is aligned with the supports between a ring's slots, as shown. The affected slots on the side closer to the hard surface 250 are compressed 246 while the affected slots on the opposite side are expanded 248. This causes the outer annulus 252 to shift away from the hard surface on the opposite side where the deflection can be measured as with the LVDT 240 which is shown in FIG. 41.

Figure 45:
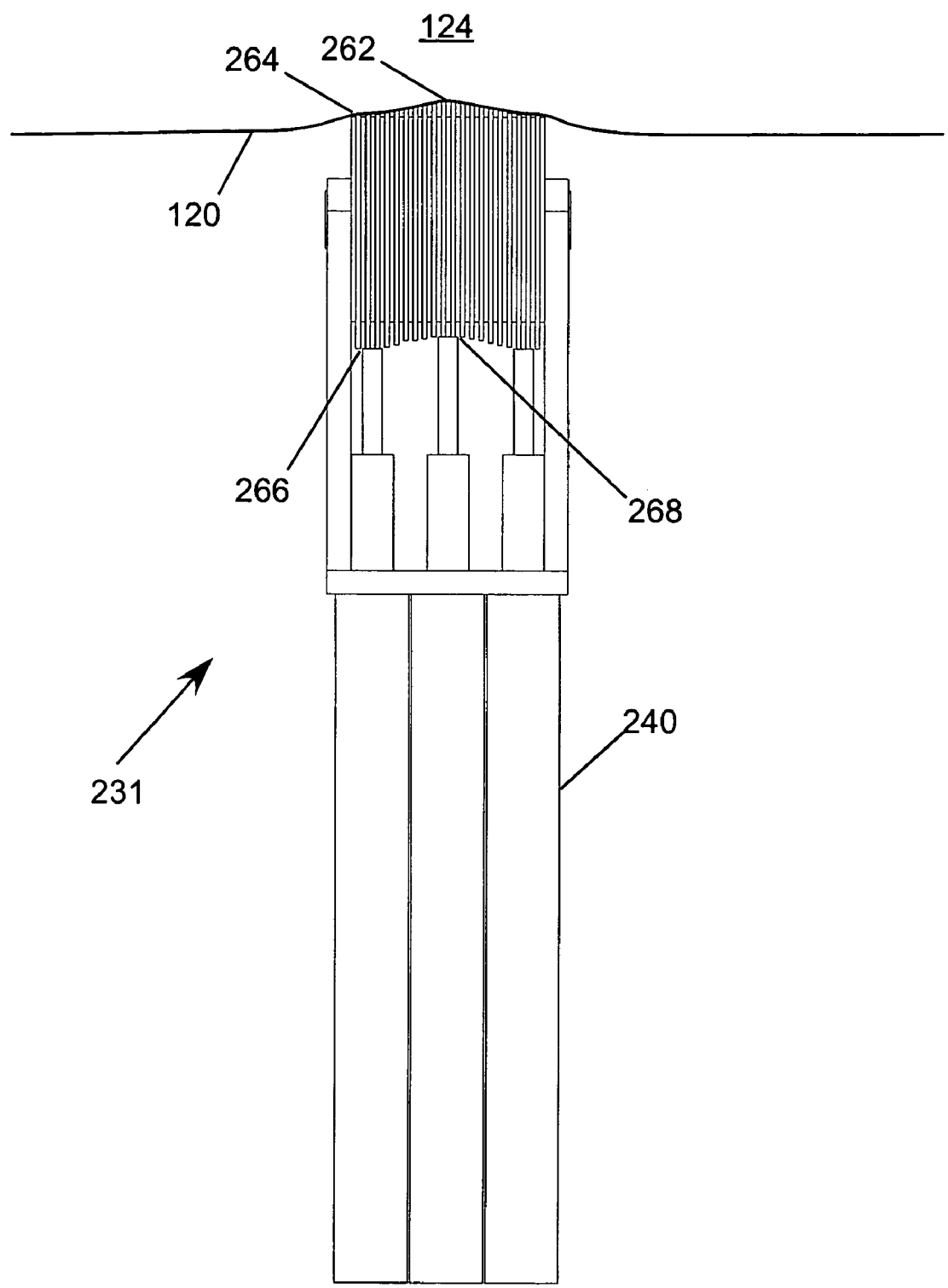
FIG. 45 is an orthogonal view of the Thin Maze Wheel assembly of FIGS. 41 to 44 pushed into soft sample.

FIG. 45 shows how the greater deformations of the thin maze wheels at the periphery 264 (compared to the center 262) of the assembly 231 cause the center of the assembly 231 to protrude farther into the soft sample 124 through the sample's skin 120. This deformation differential can be measured at the backside by the LVDT's 240. The LVDT at the periphery 266 is displaced more than the LVDT at the center 268. The more continuous conforming nature of this stack of many thin maze wheels 242 will be more comfortable to a sensitive sample.

Figures 48, 49:
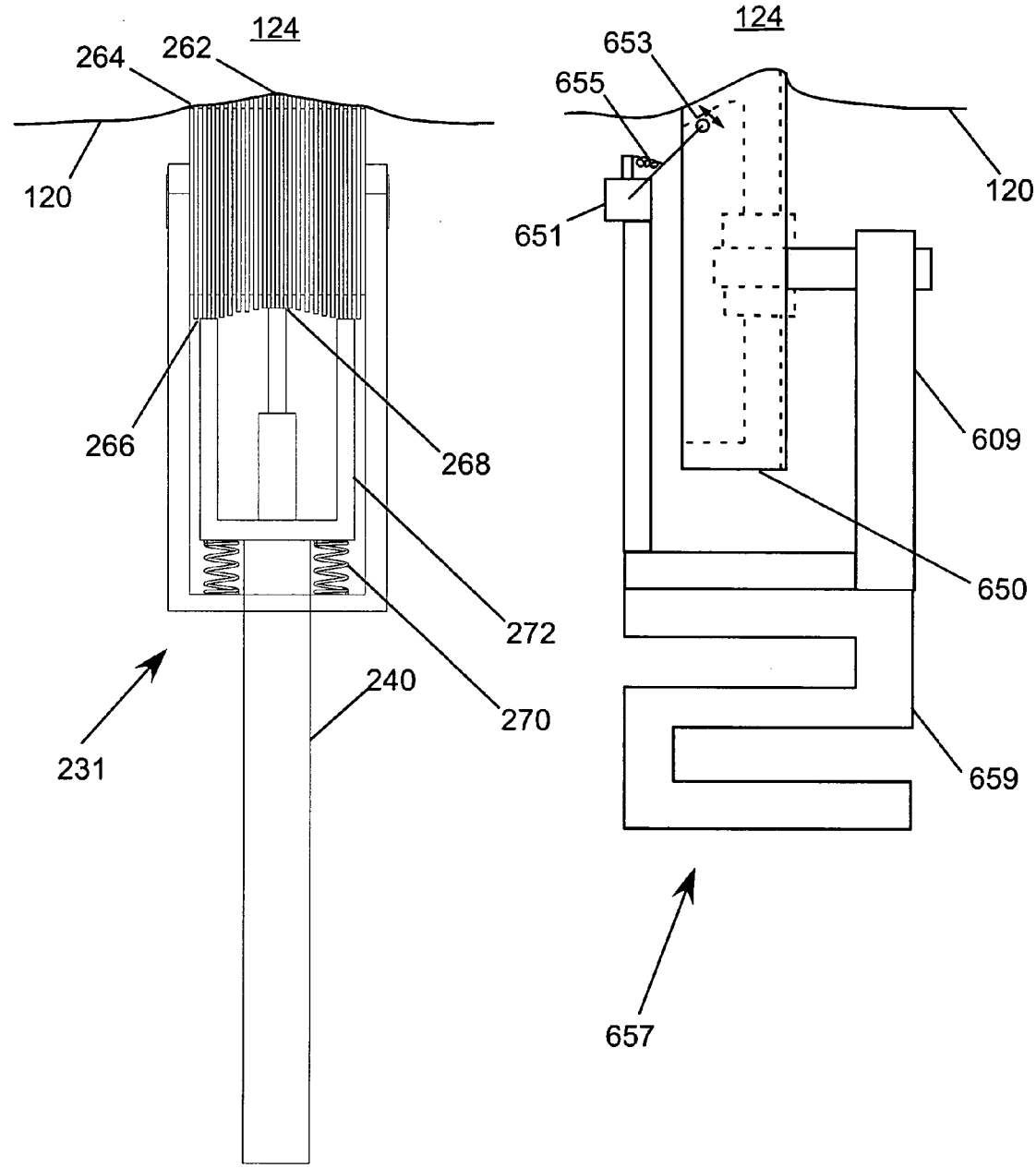
FIG. 48 is an orthogonal view of the Thin Maze Wheel assembly of FIGS. 41 to 46 with a single displacement sensor measuring differential between center and peripheral thin maze wheel deformations.
FIG. 49 is an orthogonal view of a Unilateral Bending Wheel assembly pressing into a soft (fleshy) area of a sample and with an external deformation sensor.

FIG. 48 demonstrates that the assembly needs only to detect the differential in deformation between the center and peripheral portions of the contact patch. A configuration may be devised whereby a single displacement sensor 240 can be mounted with its two reference locations spanning the center and peripheral thin maze wheel deformation positions. This figure shows the actuator coupled to the back of the center portion of the thin maze wheel spindle 268 while the LVDT's body 240 is coupled to the two peripheral sections of the thin maze wheel spindle 266 by a connecting bracket 272. The entire sensing assembly is kept in contact with the thin maze wheel spindle by use of springs 270. This would make the apparatus insensitive to overall pressure being applied to the sample but that measurement may be made externally if needed.

The LVDT's 240 may be replaced a measuring system which measures the displacement of the thin maze wheels 242 at more points, potentially, the displacement of each thin maze wheel 242 may be measured. For example, a contact image sensor and illuminator could measure reflected light off the backside of each thin maze wheel 242 with a pixel dedicated to each wheel and appropriate masking geometry to ensure that each pixel sees reflections from mostly the one wheel it is measuring.

The data flow diagram shown in FIG. 34 also applies to both the Thick Maze Wheel and the Thin Maze Wheel embodiments.

This type of implementation is particularly favored if the controller wishes to not only measure local firmness but also detect boundaries or gradients of firmness. As shown in FIG. 46, when the Thin Maze Wheel assembly 231 is pressed into a sample bridging a soft 124 and firm 122 area, the thin maze wheels pressed into the firmer area 122 will deform further away from the sample 264 than the part pressing into the softer area 262. A displacement sensor measuring this deformation can thereby detect the asymmetry and locate the boundary between the soft and firm areas of the sample.

The data flow diagram shown in FIG. 47 can be used to identify/locate a boundary or gradient in sample firmness. The outputs 750 and 758, respectively, from the peripheral displacement sensor 110 (in the example of FIG. 46, this would be a peripheral LVDT 266) and central displacement sensor 111 (in this example, this would be a central LVDT 268) is differenced 756. This result 754 is then divided 762 by the sum 767 of these two outputs. The quotient 766 is then passed to the controller 768 which interprets the result. This controller 768 could thereby determine the presence and magnitude of the firmness gradient. Another implementation which reduces the number of sensors as in FIG. 48 would be a Unilateral Bending Wheel embodiment as shown in FIG. 49 where the sensor is mounted to the bracket 609 and by means of a displacement sensor 651 coupled to the inside of one side of the bending wheel 650 via sliding or rolling contact 653. For example, a rotary potentiometer 651 with a lubricious tip 653 touching the inside of the bending portion of the wheel 650 can detect the degree of wheel deformation. A spring 655 keeps the sensor tip 653 in contact with the bending wheel 650. Optionally, a load cell 659 mounted to the assembly 657 can measure the overall pressure exerted on the sample. The combination of the load cell 659 and displacement sensor 651 outputs can be used to determine sample firmness.

From the foregoing disclosure and detailed description of certain preferred embodiments, it is apparent that disclosed embodiments of the present invention provide firmness measurement of "un-sandwiched" samples with rolling contact and seek to measure the firmness of a local area of a sample, not just locate the boundaries or gradients thereof. It is also apparent that the disclosed embodiments of the present invention include the combination of rolling contact and a firmness gauge which measures a force/displacement differential across a contact area.

This application has described four embodiments—the Tri-Wheel, Tread Wheel, Bending Wheel, and Maze Wheel—which allow measurement of sample firmness with rolling contact while not requiring the sample to be fixtured or otherwise restrained and while being relatively insensitive to movement of the sample away from the measurement device. There exist additional embodiments which operate similarly with a different configuration and it is the intention of this application to claim such devices which use methods fall within the scope of the claims below.

What is claimed is:

1. An apparatus for determining the localized firmness of a sample, said apparatus comprising:
   at least one indenter engaging the sample at an area of contact and in rolling contact with the sample so that the area of contact moves along the sample as the indenter rolls along the sample; and
   sensing means for measuring differential of at least one of:
   (a) a reactive force across the area of contact of the sample against the indenter and indicating localized firmness of the sample, and
   (b) a reactive displacement across the area of contact of the indenter away from the sample and indicating localized firmness of the sample;
   wherein said apparatus contacts the sample from only one side of the sample;
   wherein the said apparatus measures localized firmness of homogenous samples and inhomogenous samples.

2. The apparatus according to claim 1, wherein the sensing means communicates directly with the sample.

3. The apparatus according to claim 1, wherein the sensing means communicates with the sample through at least one flexible membrane.

4. The apparatus according to claim 1, whereby the apparatus is insensitive to displacement and gross deformation of the sample.

5. The apparatus according to claim 1, wherein the sensing means includes at least three sensing mechanisms, each sensing mechanism coupled to the sample by adjacent rolling contact, and each sensing mechanism resolving at least one of force and displacement.

6. The apparatus according to claim 1, wherein the indenter presses into the sample at a center sensing area of the sample and at least one peripheral sensing area of the sample surrounding the center sensing area on at least two sides such that the center and peripheral sensing areas are proximate to each other so that deflection of each of the center and peripheral sensing areas into the sample affects a force-displacement curve of at least one of the other sensing areas, and the sensing means measures differential between reactive displacement of the center sensing area and the peripheral sensing area to determine sample firmness.

7. The apparatus according to claim 1, wherein the indenter presses into the sample at a center sensing area of the sample and at least one peripheral sensing area of the sample surrounding the center sensing area on at least two sides such that the center and peripheral sensing areas are proximate to each other so that deflection of each of the center and peripheral sensing areas into the sample affects a force-displacement curve of at least one of the other sensing areas, and the sensing means measures differential between reactive force of the center sensing area and the peripheral sensing area to determine sample firmness.

8. The apparatus according to claim 1, wherein there are at least three of the indenters, each of the indenters is in simultaneous rolling contact with the sample, the indenters are proximate to each other so that each indenter's deflection into the sample affects a force-displacement curve of at least one of the other indenters, and at least two of the indenters have independent force-displacement measurement means.

9. The apparatus according to claim 1, wherein there are at least three of the indenters, each of the indenters is in simultaneous rolling contact with the sample, each of the indenters is mounted so that rolling paths of contact on the sample are approximately parallel, the indenters are proximate to each other so that each indenter's deflection into the sample affects a force-displacement curve of at least one of the other indenters, and at least two of the indenters have independent force-displacement measurement means.

10. The apparatus according to claim 1, wherein there is a single indenter, the sensor means comprises at least three force sensing areas on the single rolling indenter, each of the force sensing areas is in simultaneous rolling contact with a surface of the sample, and the force sensing area are proximate to each other so that each area's movement into the sample affects a force-displacement curve of at least one of the other sensing areas.

11. The apparatus according to claim 1, wherein there is single indenter, the sensing means comprises at least three force sensing areas on the single rolling indenter, each of the force sensing areas is in simultaneous rolling contact with a surface of the sample, the force sensing areas are proximate to each other so that each sensing area's movement into the sample affects a force-displacement curve of at least one of the other sensing areas, and each of the force sensing areas is mounted along a stripe spanning the circumference of the single rolling indenter.

12. The apparatus according to claim 1, wherein there is a single indenter, the sensing means comprises at least three force sensing areas on the single rolling indenter, each of the force sensing areas is in simultaneous rolling contact with a surface of the sample, the force sensing areas are proximate to each other so that each sensing area's movement into the sample affects a force-displacement curve of at least one of the other sensing areas, each of the force sensing areas is mounted along a stripe spanning the circumference of the rolling indenter, and the force sensing areas span a width of a contact patch of the indenter.

13. The apparatus according to claim 1, wherein the indenter includes a rolling wheel capable of deforming across a contact patch when pressed into the sample, a degree of deformation of the rolling wheel is related to firmness of the sample and the sensing means include a sensor capable of measuring the degree of deformation.

14. The apparatus according to claim 1, wherein the indenter includes a rolling wheel capable of deforming across a contact patch when pressed into the sample, a degree of deformation of the rolling wheel is related to firmness of the sample, the sensing means includes a sensor capable of measuring the degree of deformation, and measured deformation is across a width of the rolling wheel.

15. The apparatus according to claim 1, wherein the indenter includes a rolling wheel capable of deforming across a contact patch when pressed into the sample, a degree of deformation of the rolling wheel is related to firmness of the sample, the sensing means includes a sensor capable of measuring the degree of deformation, and measured deformation is along a circumference of the rolling wheel.

16. The apparatus according to claim 1, wherein the indenter includes a spindle of at least three discs, each of the discs is capable of deforming when pressed into the sample such that an outer ring remains approximately round with deformation causing the outer ring of the disc to move away from contact patch of the sample, and the discs are proximate to each other so that movement into the sample by each of the discs affects a reactive force seen by at least one of the other discs.

17. The apparatus according to claim 1, wherein the indenter includes a spindle of at least three discs, each of the discs is capable of deforming when pressed into the sample such that an outer ring remains approximately round with the deformation causing the outer ring to move away from contact patch of the sample, the discs are proximate to each other so that movement into the sample by each of the discs affects a reactive force seen by at least one of the other discs, and the sensing means includes at least one sensor capable of measuring a differential in deformation away from the sample of at least two of the discs.

18. An apparatus for locating gradients of firmness of a sample, said apparatus comprising:
  at least one indenter engaging the sample at an area of contact and in rolling contact with the sample so that the area of contact moves along the sample as the indenter rolls along the sample; and
  sensing means for measuring differential of at least one of:
    (a) a reactive force across the area of contact of the sample against the indenter and indicating localized firmness of the sample, and
    (b) a reactive displacement across the area of contact of the indenter away from the sample and indicating localized firmness of the sample;
  wherein said apparatus contacts the sample from only one side of the sample;
  wherein said apparatus measures localized firmness of homogenous samples and inhomogenous samples.

19. An apparatus for determining the localized firmness of a sample, said apparatus comprising:
  at least one indenter engaging the sample at an area of contact and in rolling contact with the sample so that the area of contact moves along the sample as the indenter rolls along the sample; and
  at least one sensor measuring differential of at least one of:
    (a) a reactive force across the area of contact of the sample against the indenter and indicating localized firmness of the sample, and
    (b) a reactive displacement across the area of contact of the indenter away from the sample and indicating localized firmness of the sample;
  wherein said apparatus contacts the sample from only one side of the sample;
  wherein said apparatus measures localized firmness of homogenous samples and inhomogenous samples.

* * * * *